(12) United States Patent
Good et al.

(10) Patent No.: US 7,888,066 B2
(45) Date of Patent: Feb. 15, 2011

(54) METHODS FOR IDENTIFYING SUBSTANCES FOR THE TREATMENT OF ALZHEIMER'S DISEASE

(75) Inventors: Paul F. Good, Chappaqua, NY (US); Stave D. Kohtz, New York, NY (US)

(73) Assignee: Mount Sinai School of Medicine, New York, NY (US)

( * ) Notice: Subject to any disclaimer, the term of this patent is extended or adjusted under 35 U.S.C. 154(b) by 0 days.

(21) Appl. No.: 12/353,196

(22) Filed: Jan. 13, 2009

(65) Prior Publication Data
US 2009/0136990 A1 May 28, 2009

Related U.S. Application Data

(60) Continuation of application No. 11/147,022, filed on Jun. 6, 2005, now abandoned, which is a division of application No. 10/200,001, filed on Jul. 19, 2002, now abandoned.

(60) Provisional application No. 60/306,827, filed on Jul. 20, 2001.

(51) Int. Cl.
*C12P 21/06* (2006.01)
*C07K 14/00* (2006.01)

(52) U.S. Cl. .................. 435/69.1; 530/350; 530/839

(58) Field of Classification Search ................ None
See application file for complete search history.

(56) References Cited

U.S. PATENT DOCUMENTS

| | | | | |
|---|---|---|---|---|
| 5,416,197 | A * | 5/1995 | Raper et al. | 530/387.9 |
| 5,639,856 | A | 6/1997 | Goodman et al. | |
| 6,054,293 | A | 4/2000 | Tessiser-Lavigne | |
| 6,335,170 | B1 | 1/2002 | Orntoft et al. | |
| 6,428,965 | B1 | 8/2002 | Ginty et al. | |
| 2001/0049432 | A1 | 12/2001 | Holloway | |

FOREIGN PATENT DOCUMENTS

WO   WO 01/18173   *   3/2001

OTHER PUBLICATIONS

Giger et al., "Anatomical distribution of the chemorepellent semaphorin III/collapsin-1 in the adult rat and human brain: predominant expression in structures of the olfactory-hippocampal pathway and the motor system" J. Neurosci. Res. 1998; 52:27-42.
Gagliardini et al., "Semaphorin III Can Induce Death in Sensory Neurons" Mol. Cell Neurosci. 1999; 14:301-316.
Shirvan et al., "Semaphorins as Mediators of Neuronal Apoptosis" J. Neurochemistry 1999; 73:961-71.
Arimura et al., "Phosphorylation of collapsin response mediator protein-2 by Rho-kinase. Evidence for two separate signaling pathways for growth cone collapse.", J. Biological Chemistry 2000; 275:23973-80.
Bagnard et al., "Semaphorin 3A-vascular endothelial growth factor-165 balance mediates migration and apoptosis of neural progenitor cells by the recruitment of shared receptor", Neurosci 2001: 21(10):3332-41.
Ferrer et al., "Phosphorylated mitogen-activated protein kinase (MAPK/ERK-P), protein kinase of 38kDa (p38-P), stress-activated protein kinase (SAPK/JNK-P), and calcium/calmodulin-dependent kinase II (CaM kinase II) are differentially expressed in tau deposits in ne", J. Neural Tranm. 2001; 108(12):1397-1415.
Gavazzi et al., "Semaphorin-neuropilin-1 interactions in plasticity and regeneration of adult neurons.", Cell Tissue Research 2001; 305:275-84.
Loes, et al. "Expression of Class 3 Semaphorins and Neuropilin Receptors in the Developing Mouse Tooth." Mechanisms of Development, Mar. 2001, vol. 101, No. 1-2, pp. 191-194.
Barzilai, et al. "The Molecular Mechanism of Dopamine-Induced Apoptosis: Identification and Characterization of Genes That Mediate Dopamine Toxicity." Journal of Neural Transmission, vol. 60, Supplement, pp. 59-76.
Good, et al. "A Role for Semaphorin 3A Signaling in the Degeneration of Hippocampal Neurons During Alzheimer's Disease." Society for Neuroscience Abstract Viewer and Itinerant Planner, vol. 2002, Abstract No. 328.8.
Takao, et al. "Neuroprotective Effects of Vascular Endothelial Growth Factor (VEGF) Upon Dopaminergic Neruons in a Rat Model of Parkinson's Disease." European Journal of Neuroscience, vol. 19, No. 6, Mar. 2004, pp. 1494-1504.
Ren, et al. "Expression of Competent Semaphorin Receptors in the Developing and Adult Nigrostriatal Pathway." Experimental Neurology, vol. 187, No. 1, May 2004, p. 217FF.
Semaphorin Nomenclature Committee: Unified nonmenclature for the semaphorins/collapsins, Cell (1999), 97:551-552.
Raper, Jonathan A., Semaphorins and their receptors in vertebrates and invertebrates, Current Opinion in Neurobiology (2000), 10:88-94.
Pasterkamp, Jeroen R. and Kolodkin, Alex L., Semaphorin junction: making tracks toward neural connectivity, Current Opinion in Neurobiology (2003), 13:79-89.
Yazdani, Umar and Terman, Jonathan R., The semaphorins, Genome Biology (2006), 7:211.1-211.14.
Fumio Nakamura, et. al., "Molecular Basis of Semaphorin-Mediated Axon Guidance"; *J. Neurobiol.* 2000; 44(2):219-29.
Hong-jun Song, et al., "Conversion of Neuronal Growth Cone Responses from Repulsion to Attraction by Cyclic Nucleotides"; *Science* 1998; 281: 1515-18.

* cited by examiner

*Primary Examiner*—Jeffrey Stucker
*Assistant Examiner*—Aditi Dutt
(74) *Attorney, Agent, or Firm*—Fish & Richardson P.C.

(57) ABSTRACT

The present invention relates to a method for diagnosing Alzheimer's disease and Parkinson's disease in a subject by analyzing the expression of Semaphorin 3 and downstream effectors. It also provides a method for identifying a substance useful in the prevention or treatment of Alzheimer's disease and Parkinson's disease, and a method of using such substance in the treatment of Alzheimer's disease and Parkinson's disease.

2 Claims, 5 Drawing Sheets

```
                              SEQUENCE LISTING

<160> NUMBER OF SEQ ID NOS: 1

<210> SEQ ID NO 1
<211> LENGTH: 15
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: Xaa is phosphorylated Threonin

<400> SEQUENCE: 1

Ile Tyr Ser Tyr Gln Trp Met Ala Leu Xaa Pro Val Val Lys Cys
1               5                   10                  15
```

METHODS FOR IDENTIFYING SUBSTANCES FOR THE TREATMENT OF ALZHEIMER'S DISEASE

The present application is a continuation of U.S. patent application Ser. No. 11/147,022, filed Jun. 6, 2005, now abandoned, which is divisional of U.S. patent application Ser. No. 10/200,001, filed Jul. 19, 2002, now abandoned, which claims priority from U.S. Provisional Patent Application Ser. No. 60/306,827, filed Jul. 20, 2001, the disclosures of which are hereby incorporated by reference in their entirety.

FIELD OF THE INVENTION

The present invention relates to a method for diagnosing Alzheimer's disease and Parkinson's disease in a subject by analyzing the expression of Semaphorin 3 and downstream effectors. It also provides a method for identifying a substance useful in the prevention or treatment of Alzheimer's disease and Parkinson's disease, and a method of using such substance in the treatment of Alzheimer's disease and Parkinson's disease.

BACKGROUND OF THE INVENTION

Axonal guidance occurs through the complex interplay of chemoattractant and chemorepellant factors that are capable of either guiding the growth cone toward an appropriate target or repelling a growth cone by causing it to collapse, such that innervation of inappropriate targets does not occur. One molecular mechanism responsible for such growth cone repulsion is signaling by semaphorins (Mark et al., Cell Tissues Res. 1997; 290(2): 2661-8; Raper, Curr. Opin Neurobiol, 2000; 10(1): 88-94). Semaphorins play a central role in mediating neuronal plasticity during embryonic development by acting as repulsive axonal guidance signals inducing collapse of growth cones (Puschel, Eur J Neurosci 1996; 8:1317-1321; Raper, Curr Opin Neurobiol 2000; 10:88-94).

As either a cell surface or secreted protein, Semaphorin 3A (Sema 3A) mediated by the intracellular effector, collapsin response mediator protein (CRMP), Quin et al., J Neurobiol 1999; 41(1): 158-64; Wang et al., J Neurosci 1996; 16(19): 6197-207), produces repulsive guidance by the reversible collapse of growth cones. An important element of the effects of Sema3A signaling is the role that it may play in regulating the neuronal population in the developing nervous system, matching afferent innervation to target requirements, resulting in programmed cell death of afferent neurons. It has been demonstrated in neural progenitor cells (Bagnard et al., J Neurosci 2001; 21(10): 3332-41), sensory (Gagliardini and Fankhauser, Mol Cell Neurosci 1999; 14:301-316), sympathetic, and cerebellar granule neurons (Shirvan et al., J Neurochemistry 1999; 73:961-71), known to express Sema3A in the developing nervous system, that administration of Sema3A in culture induces morphological and biochemical evidence of programmed cell death and apoptosis, resulting in neurodegeneration. A critical aspect of the studies by Shirvan and co-workers is the use of the model of dopamine induced oxidative stress, in which they identified the upregulation of both Semaphorin and CRMP-2, coincident with the induction of apoptosis in sympathetic neuronal cultures.

The chemorepulsive effects of Sema3A are transduced by a receptor complex containing the transmembrane proteins Neuropilin-1 and Plexin A1 or A2 (Takahashi et al., Cell 1999; 99:59-69; Rohm et al., Mech Dev 2000; 93:95-104), and the intracellular effector molecule collapsin response mediator protein 2 (CRMP-2) (Wang and Strittmatter, J Neurosci 1996; 16:6197-6207). Microinjection of the chick CRMP-2 homolog, CRM62, neutralizing antibodies into chick dorsal root ganglion has been shown to block chicken Sema3A-induced growth cone collapse, suggesting a direct role for CRMP-2 in Sema3A signaling cascades (Goshima et al., Nature 1995; 376:509-14).

The expression of phosphorylated p38, a downstream kinase of the mitogen-activated extracellular signal-regulated protein kinase, has also been examined in AD (Ferrer et al., J Neural Transam 2001; 108(12):1397-1415; Atorzi et al., J Neuropathol Exp Neurol 2001; 60(12):1190-97) and PD (Ferrer et al., J Neural Transm 2001; 108(120:1383-96). Immunohistochemical analysis revealed strong staining of phosphorylated p38 in about 50-70% of neurons with neurofibrillary tangles, and neuronal or glial cells that contained tau-positive deposits in both AD and PD. Both AD and PD are characterized by intracellular deposits of hyperphosphorylated tau, a microtubule-associated protein that is responsible for the formation of neurofibrillary tangles. However, in both AD and PD, analysis of apoptosis-related changes including DNA fragmentation, demonstrated that the expression of p38 was unrelated to activation of an apoptotic cascade.

Alzheimer's Disease

Alzheimer's Disease ("AD") is a dementing disorder characterized by progressive impairments in memory and cognition. It typically occurs in later life, and is associated with a multiplicity of structural, chemical and functional abnormalities involving brain regions concerned with cognition and memory. This form of dementia was first reported by Alois Alzheimer in 1907 when he described a disease of the cerebral cortex in a 51-year-old woman suffering from an inexorably progressive dementing disorder. Although other forms of dementia had been well characterized at the time of Alzheimer's clinical report, his patient was clinically and pathologically unusual, because of her relatively young age and the presence of the then newly described intra-cellular inclusions which have subsequently come to be known as neurofibrillary tangles (NFTs). In recognition of this unique combination of clinical and pathological features, the term "Alzheimer's Disease (AD)" subsequently came into common usage.

In spite of the many research investigations and diverse studies undertaken to date, present clinical evaluations still cannot establish an unequivocal diagnosis of AD. To the contrary, the only presently known means for positively proving and demonstrating AD in a patient can only be achieved by a brain biopsy or a postmortem examination to assess and determine the presence of NFTs and senile (amyloid) plaques in brain tissue.

Instead, a set of psychological criteria for the diagnosis of probable AD has been described, and includes the presence of a dementia syndrome with defects in two or more areas of cognition, and progressive worsening of memory and other cognitive function over time. However, by the time these psychological changes may be observed, significant irreversible neuronal damage has already occurred.

It is therefore clear that there has been and remains today a long standing need for an accurate and reliable test to diagnose AD in a living human subject before the disease has manifested far enough to produce psychological changes, thereby allowing earlier and more effective therapeutic intervention.

Furthermore, only a limited number of pharmacological agents heretofore have been identified as effective in treating symptoms of AD in a person suffering therefrom. The most prominent of these today are tacrine and donepezil hydrochloride, which are cholinesterase inhibitors active in the brain. These drugs do not slow the progress of the disease. Furthermore no compound has been established as effective in blocking the development or progression of AD although a number of compounds, including estrogen, ibuprofen, selegiline, are thought to possibly have this capability and are being investigated for therapeutic use for this purpose.

Parkinson's Disease

Parkinson's disease ("PD") is a chronic nervous disease characterized by fine, slowly spreading tremors, rigidity, and a characteristic gait. Although the onset of PD may be abrupt, it generally occurs gradually. The initial symptom is often a fine tremor beginning in either a hand or a foot which may spread until it involves all of the members. The duration of PD is indefinite, and recovery rarely if ever occurs. A psychotic confusional state may be seen in the later stages of PD, which is a common and significant source of morbidity.

L-dopamine has historically been the medication of choice in treating PD, and there are rarely any failures with L-dopamine therapy in the early years of treatment. Unfortunately, this response is not sustainable. Most patients regress after long-term usage of L-dopamine; in fact, in some the benefits of treatment wane as the disease progresses.

Several common types of central nervous system dysfunction and peripheral side effects are associated with administration of L-dopamine. Toxic side effects to the central nervous system include mental changes, such as confusion, agitation, hallucinosis, hallucinations, delusions, depression, mania and excessive sleeping. The symptoms may be related to activation of dopamine receptors in non-striatal regions, particularly the cortical and limbic structures. Elderly patients and patients with cortical Lewy body disease or concomitant AD are extremely sensitive to small doses of L-dopamine. Moreover, all patients with PD, regardless of age, can develop psychosis if they take excess amounts of L-dopamine as a means to overcome "off" periods. This is difficult to remedy, as reducing the dosage of L-dopamine may lessen its beneficial influence on motor function.

Prior to the introduction of L-dopamine, anticholinergic drugs had been the conventional treatment of mild Parkinsonism since the discovery of belladonna alkaloids in the mid-nineteenth century. However, these drugs have a propensity for exacerbating dementia. Nevertheless, since anticholinergic drugs are known to ameliorate rigidity in the early stages of the disease, the conventionally skilled neurologist would instinctively believe that a procholineric drug might worsen rigidity, as central cholinergic activity appears to be important for memory function in PD. Unfortunately, patients receiving anticholinergic drugs for Parkinsonism may experience reversible cognitive deficits so severe as to mimic AD. Identical memory disturbances have been produced by administration of atropine to patients with either AD or PD with dementia.

The substantia nigra lies in the midbrain immediately dorsal to the cerebral peduncles. The substantia nigra is thought to be the lesion site in PD or paralysis agitans. The mechanism of neurodegeneration of substantia nigra neurons in PD is unknown. The most consistent pathological finding in PD is degeneration of the melanin-containing cells in the pars compacta (another part is called the pars reticulata) of the substantia nigra (melanin is an inert by-product of the synthesis of dopamine). As mentioned above, cells within the nigra produce dopamine normally. This substance passes, via axoplasmic flow, to the nerve terminals in the striatum (caudate nucleus and putamen), where it is released as a transmitter. It is the absence of this transmitter that produces the crippling disorder. It is believed that the cellular apparatus associated with programmed cell death and apoptosis may play a key role in the neurodegenerative cascade. Although this is a significant prospect, the mechanisms that lead to the induction of programmed cell death pathways are unclear. A hypothesis presented herein identifies the reactivation of embryonic developmental mechanisms in the adult central nervous system with the induction of programmed cell death.

Amyotrophic Lateral Sclerosis

Amyotrophic lateral sclerosis ("ALS"), also called Lou Gehrig's disease, is a progressive, fatal neurological disease affecting as many as 20,000 Americans with 5,000 new cases occurring in the United States each year. The disorder belongs to a class of disorders known as motor neuron diseases. ALS occurs when specific nerve cells in the brain and spinal cord that control voluntary movement gradually degenerate. Both the brain and spinal cord lose the ability to initiate and send messages to the muscles in the body. The muscles, which are unable to function, gradually atrophy and twitch.

ALS manifests itself in different ways, depending on which muscles weaken first. Symptoms may include tripping and falling, loss of motor control in hands and arms, difficulty speaking, swallowing and/or breathing, persistent fatigue, and twitching and cramping, sometimes quite severely. Eventually, when the muscles in the diaphragm and chest wall become too weak, patients require a ventilator to breathe. Most people with ALS die from respiratory failure, usually 3 to 5 years after being diagnosed; however, some people survive 10 or more years after diagnosis. ALS strikes in mid-life. Men are about one-and-a-half times more likely to the disease than women.

There is no cure for ALS, nor is there a proven therapy that will prevent or reverse the course of the disorder. The Food and Drug Administration (FDA) recently approved riluzole, the first drug that has been shown to prolong the survival of ALS patients. Patients may also receive supportive treatments that address some of their symptoms.

Thus, there is a need in the art of more effective treatments for neurodegenerative diseases such as AD, PD, and ALS.

SUMMARY OF THE INVENTION

The present invention also is based on the discovery of a Semaphorin 3 pathway as a target for diagnosis, prevention and treatment of AD and PD.

The present invention thus contemplates a method for diagnosing AD and PD in a subject, which method comprises assessing the level of expression, accumulation or activity of Sema3A, or members of the Sema3A downstream signaling complex, in a test subject, and comparing it to the level of expression, accumulation or activity of Sema3A, or Sema3A effectors, in a control subject, wherein an increase of expression, accumulation or activity of Sema3A or signaling complex members in the test subject compared to the control subject is indicative of AD or PD disease in the test subject. This method is particularly useful for early diagnosis of AD and PD, preferably when the test subject is asymptomatic for AD or PD. This method may also involve examining co-expression of abnormally phosphorylated proteins specific to each disease i.e., phosphorylated tau and phosphorylated α-synuclein for AD.

The method may be performed in vitro by assessing the level of expression, accumulation or activity of Sema3A in a biological sample, such as blood, serum, cerebrospinal fluid (CSF), or neuronal tissue.

The level of expression or accumulation of Sema3A may be assessed preferably by determining the quantity of Sema3A protein present in the biological sample, or alternatively by assaying the quantity of mRNA present in the biological sample that encodes Sema3A.

In a preferred embodiment, the determination of the quantity of Semaphorin 3A protein present in the biological sample is effected by an immunoassay using an antibody directed against Sema3A. Such an immunoassay involve contacting the biological sample with a detectably labeled antibody which is directed against Sema3A under conditions and time sufficient to allow the formation of complexes between the antibody and Sema3A potentially present in the biological sample. Then, one proceeds to detect and measure the level of formation of these complexes.

In another embodiment the level of activity of Sema3A is assessed by determining the level of expression or activity of an effector protein downstream the Semaphorin 3A pathway, such as an effector selected from the group consisting of MAP1B, CRMP-2, Plexins A1 and A2, Neuropilin 1 and Rac1. In a variation of the immunoassay described supra, the biological sample is contacted with a second antibody directed against a downstream effector of Sema3A, either together with the anti-Sema3A antibody, or sequentially (i.e., before or after).

The present invention further contemplates a method for identifying a substance useful in the prevention or treatment of AD or PD, which method comprises determining the effect of the substance on a biological activity of Sema3A, wherein an inhibitory effect is indicative of a substance useful in the prevention or treatment of AD or PD.

This method may be performed in vitro, or in vivo by administering the substance to an animal that shows a level of Sema3A protein superior to a control animal.

In one embodiment of this screening method, the determination of the effect of the substance on the biological activity of Sema3A proceeds by contacting a test cell with the substance and Sema3A under conditions wherein addition of Sema3A alone induces apoptosis of the cell. One then observes the effect of addition of the substance and Sema3A on the cell, in comparison with the effect of addition of Sema3A alone on a control cell, wherein inhibition of apoptosis of the test cell compared to the control cell is indicative of a substance useful in the prevention or treatment of AD or PD.

The cell used in the initial step may be of any appropriate type, and is preferably a neuronal cell.

In another embodiment of this screening method, the determination of the effect of the substance on the biological activity of Sema3A involves contacting a test neuronal cell with the substance and Sema3A under conditions wherein addition of Sema3A alone induces withdrawal of the nerve growth cone. This is followed by observing the effect of the addition of the substance and Sema3A on the test cell, in comparison with the effect of addition of Sema3A alone on a control cell, wherein inhibition of withdrawal of the nerve growth cone in the test cell compared to the control cell is indicative of a substance useful in the prevention or treatment of AD.

In still another embodiment of this screening method, the determination of the effect of the substance on the biological activity of Sema3A comprises determining the effect of the substance on the binding or activation of Sema3A receptor by Sema3A, wherein an antagonist effect indicates that the substance is useful in the prevention or treatment of AD or PD.

A further subject of the present invention is a method for the prevention or treatment of AD or PD, which method comprises administering to a patient in need of such treatment an effective amount of a substance that inhibits Sema3A expression, accumulation or activity, which a pharmaceutically acceptable carrier. For example this inhibitory substance may be an antibody directed against Sema3A, or an antisense nucleic acid specific for Sema3A mRNA, or the mRNA of one of the downstream effectors in the Sema3A signaling pathway.

The above embodiments may also apply to other neurodegenerative diseases, or conditions where neurons are damaged or injured, such as ALS and stroke.

DESCRIPTION OF THE DRAWINGS

FIG. 1A: Photomontage of anti-Sema 3A immunoglobulin of an 82 year-old CDR0 case comprising hippocampus subfields CA2/3 and CA1. Arrows indicate transitions between CA3, CA2 and CA1. FIG. 1B: higher magnification of CA1 at CA2 border (area indicated by box, FIG. 1A). Note lightly labeled neurons. FIG. 1C: cubiculum of this case, neurons are unlabeled. FIG. 1D: Sema 3A immunoglobulin of a 64 year-old AD case; arrows indicate transitions as in FIG. 1A. FIG. 1E: CA1 (box, FIG. 1D) neurons are all intensely labeled. FIG. 1F: cubiculum of the same case, a number of neurons demonstrate Sema 3A immunoreactivity. FIG. 1G: Photomontage of an 86 year-old CDR 5 case; arrows indicate transitions as in FIG. 1A. CA1 proximal to CA2 (box, FIG. 1G) demonstrates intense immunolabeling of large, vesicular, intra- and extracellular profiles (FIG. 1H). Much of the remainder of CA1 appears unlabeled; in this severe AD case the majority of neurons in this region have been lost. FIG. 1I: in the subiculum of this case many neurons are heavily labeled by anti Sema 3A. Also note extracellular labeling. Scale: A, D, G, bar=250 µM; B, C, E, F, H, I, bar=50 □m.

FIG. 2A demonstrates the dendritic form of Sema 3A wherein Sema 3A coats the dendrites in the hippocampus and is not seen in a perikaryal distribution. FIG. 2B shows the internalized form of Sema 3A in the hippocampus. FIG. 2C demonstrates the dendritic form of Sema 3A in the lateral dorsal nucleus of the thalamus. FIG. 2D demonstrates the dendritic form of Sema 3A in the ventral nuclear group of the thalamus.

DETAILED DESCRIPTION

Figure 1:
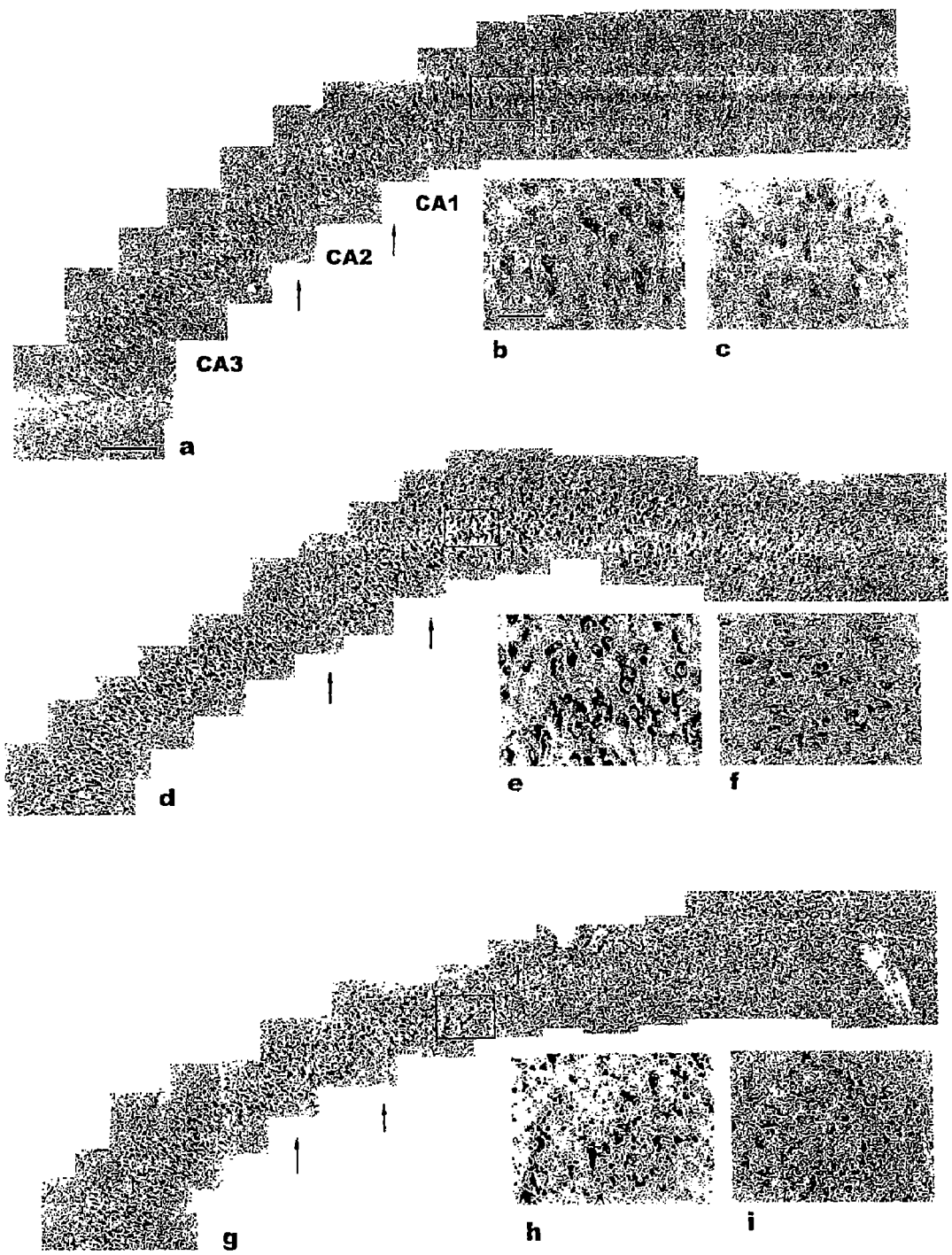
FIGS. 1A-1I show Semaphorin 3A (Sema 3A) immunoglobulin of the hippocampus tissue of CDR0 (Clinical Dementia Score), early AD and CDR5 cases with cresol violet counter stain.

To address the need in the art for more effective treatments for AD and PD, the mechanisms of neurodegeneration in AD and PD from the perspective of axonal guidance dysregulation in vulnerable hippocampal neurons was examined.

The present invention advantageously establishes that accumulation of Semaphorin 3A (Sema 3A) is enhanced during AD and PD, and that vulnerable neurons bind and internalize the active form of this protein. The invention is in part based on the surprising discovery that during progression of AD and PD, active Sema 3A signaling complexes are assembled in vulnerable neurons, and these complexes mediate the collapse, degeneration, and apoptosis of these cells.

These data provide the first evidence that Semaphorin 3A plays a major role in the development of AD and PD, and that the Semaphorin 3A pathway represents a new target for diagnosis, prevention and treatment of AD and PD. In addition, these results are suggestive of applicability to other neurodegenerative diseases involving degeneration or injury of neurons, such as amyotrophic lateral sclerosis or stroke.

DEFINITIONS

As used herein the term "Alzheimer's disease" (AD) encompasses all forms of the disease, including sporadic AD, ApoE4-related AD, other mutant APP forms of AD (e.g., mutations at APP717, which are the most common APP mutations), mutant PS1 forms of familial AD (FAD) (see, WO 96/34099), mutant PS2 forms of FAD (see, WO 97/27296), and alpha-2-macroglobulin-polymorphism-related AD.

As used herein, the term "Parkinson's disease" (PD) refers to a progressive disorder of the central nervous system (CNS), is caused by the degeneration of dopaminergic neurons in the substantia nigra of the midbrain. These neurons normally project to the striatum, consisting of the caudate and putamen nuclei, whose neurons bear dopamine receptors. This projection of neurons is just one component of the complex network of interconnections among the deep gray-matter structures known as the basal ganglia. Neurochemical or structural pathologic conditions affecting the basal ganglia result in diseases of motor control, classified as movement disorders.

The "substantia nigra" refers to a midbrain structure, is considered part of the basal ganglia complex due to its close ties with the striatum. Classically it has been divided into two components: the pars compacta (SNc), and the pars reticulata (SNr). The pars compacta is a cell-rich region that in humans is composed of large pigmented neurons. In some animals (for example, humans and squirrel monkeys) the large nigral neurons exhibit a characteristic black pigmentation; hence the origin of the structure's name ("black substance").

"Amyotrophic lateral sclerosis (ALS)" refers to a disorder of the anterior horn cells of the spinal cord and the motor cranial nuclei that leads to progressive muscle weakness and atrophy. Involvement of both upper and lower motor neurons is characteristic. Patients develop variable hyperreflexia, clonus, spasticity, extensor plantar responses, and limb or tongue fasciculations. ALS is also referred to as Lou Gehrig's disease.

The subject to whom the diagnostic or therapeutic applications of the invention are directed may be any human or animal, more particularly a mammal, preferably a human, primate or a rodent, but including, without limitation, monkeys, dogs, cats, horses, cows, pigs, sheep, goats, rabbits, guinea pigs, hamsters, mice and rats.

In a preferred embodiment of the present invention, the human subject is still asymptomatic for AD or PD, or only shows early symptoms of the disease. To facilitate differential diagnosis between AD and PD in an asymptomatic patient, one would examine the sample for the presence of other abnormally phosphorylated proteins specific to each disease i.e., phosphorylated tau for AD and phosphorylated α-synuclein for AD.

The term "Semaphorin 3A protein" or "Sema3A protein" encompasses the Semaphorin protein of human origin, which has an amino acid sequence available on Swissprot database (access number for the Semaphorin 3A precursor: Q14563). It also encompasses function-conservative variants and homologous proteins thereof, more particularly proteins originating from different species.

As used herein the term "Semaphorin 3A nucleic acid" or "Sema3A nucleic acid" refers to a polynucleotide that encodes a Semaphorin 3A protein as above described. The nucleotide sequence encoding the human Semaphorin 3A protein is available on GenBank (Accession Number NM006080).

A "Semaphorin 3A gene" or "Sema3A gene" is used herein to refer to a portion of a DNA molecule that includes a Sema3A polypeptide coding sequence operatively associated with expression control sequences. Thus, a gene includes both transcribed and untranscribed regions. The transcribed region may include introns, which are spliced out of the mRNA, and 5'- and 3'-untranslated (UTR) sequences, along with protein coding sequences. In one embodiment, the gene can be a genomic or partial genomic sequence, in that it contains one or more introns. In another embodiment, the term gene may refer to a cDNA molecule (i.e., the coding sequence lacking introns).

The terms "Semaphorin 3A gene" or "Semaphorin 3A nucleic acid" encompass sequence-conservative variants and function-conservative variants, as well as homologous sequences, such as allelic variants or species variants (orthologs).

"Neuropilin-1" refers to a neuronal cell surface semaphorin 3 receptor glycoprotein important for axonal guidance in developing peripheral nervous system efferents. Neuropilin-1 also has been identified as a vascular endothelial growth factor (VEGF) receptor on endothelial cells. Exemplary nucleotide and amino acid sequences for human Neuropilin-1 can be found in GenBank (Accession No. XM_165547). Neuropilin-1 also includes sequence-conservative variants, function-conservative variants, and homologs, particularly orthologs.

"Plexin A1" and "Plexin A2" refer to cell surface proteins that bind to Neuropilin-1 to form functional Semaphorin receptor complexes. Exemplary nucleotide and amino acid sequences for human Plexins A1 and A2 can be found in GenBank (Accession Nos. XM_051261 and XM_114030, respectively). As one of ordinary skill in the art would appreciate, Plexin A1 and Plexin A2 also include sequence-conservative variants, function-conservative variants, and homologs, particularly orthologs.

"Microtubule-Associated Protein 1B (MAP1 B)" refers to the earliest microtubule-associated protein expressed in the developing nervous system. MAP1B remains high in adult dorsal root ganglion (DRG) neurons and sciatic nerve axons. Exemplary nucleotide and amino acid sequences for human MAP1B can be found in GenBank (Accession No. L06237). As one of ordinary skill in the art would appreciate, MAP1B also includes sequence-conservative variants, function-conservative variants, and homologs, particularly orthologs. MAP1B also includes phosphorylated and unphosphorylated forms of the protein.

"Collapsing response mediator protein-2 (CRMP-2)" refers to a major Rho-kinase substrate in the brain. CRMP-2 is enriched in the growing axons of cultured hippocampal neurons. Exemplary nucleotide and amino acid sequences for CRMP-2 can be found in GenBank (Accession No. U83278). As one of ordinary skill in the art would appreciate, CRMP-2 also includes sequence-conservative variants, function-conservative variants, and homologs, particularly orthologs.

"p38" refers to members of the MAPK family that are activated by a variety of environmental stresses and inflammatory cytokines. Stress signals are delivered to this cascade by members of small GTPases of the Rho family (Rac, Rho, Cdc42). Exemplary nucleotide and amino acid sequences for human p38 can be found in GenBank (Accession No. AF261073). As one of ordinary skill in the art would appreciate, p38 also includes sequence-conservative variants, function-conservative variants, and homologs, particularly orthologs. p38 also includes phosphorylated and unphosphorylated forms of the protein.

"Rac1" is a Rho-family GTPase that is involved in inducing actin cytoskeletal remodeling at designated sites in the cell cortex. Exemplary nucleotide and amino acid sequences for human Rac1 can be found in GenBank (Accession No. AF498964). As one of ordinary skill in the art would appreciate, Rac1 also includes sequence-conservative variants, function-conservative variants, and homologs, particularly orthologs.

Neuropilin-1, Plexins A1/A2, MAP1B, CRMP-2, p38 and Rac1 are collectively referred to herein as "downstream effectors."

Molecular Biology Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

The terms "polypeptide" and "protein" may be used herein interchangeably to refer to the gene product (or corresponding synthetic product) of a Semaphorin 3A gene. The term "protein" may also refer specifically to the polypeptide as expressed in cells.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions. A specific type of homolog is an ortholog, which refers to the corresponding (or coding sequence or gene product in another species (e.g., equine hemoglobin is an ortholog of human hemoglobin).

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95%) of the nucleotides match over the defined length of the DNA sequences, as determined by sequence comparison algorithms, such as BLAST, FASTA, DNA Strider, etc. An example of such a sequence is an allelic or species variant of the Sema3A gene. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, under conditions of low salt and denaturant concentrations, e.g., 5×SSC, 0.1% SDS, 0.25% milk, and no formamide; or 30% formamide, 5×SSC, 0.5% SDS). Moderate stringency hybridization conditions correspond to a higher $T_m$, under conditions of moderate salt and denaturant concentrations, e.g., 40% formamide, with 5× or 6×SCC. High stringency hybridization conditions correspond to the highest $T_m$, under conditions of high concentrations of salt and denaturants, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Semaphorin Class 3

Semaphorin of class 3 belongs to the Semaphorin family that comprises several molecules that exert cell-type specific effects on a wide variety of central and peripheral axons. These molecules are described in U.S. Pat. No. 5,639,856 and are reviewed in Pasterkamp et al., Brain Research Reviews, 200, 35: 36-54, as well as in Nakamura et al., Journal of Neurobiology 2000; 44:219-229; Tamagnone et al., P. M. Comoglio, 2000; 10:377-383; Roskies et al., Neuron 1998; 21:936-936; and Yu et al., Neuron 1999; 22:11-14.

More particularly Semaphorin 3A, referred to as Sema3A herein, is also known as C-Collapsin-1, Coll-1, human Sema III, mouse SemD, rat Sema III, Sema-Z1a (Semaphorin Nomenclature Committee, Cell 1999; 97:551-552). It is a secreted chemorepellent that is highly expressed in developing entorhinal and neocortical areas, but only weakly expressed in developing hippocampus (Chedotal, et al. Development 1998; 125: 4313-23).

Semaphorin 3A Expression or Accumulation

As used herein, the term "Sema3A expression" refers to the production of Sema3A protein, or mRNA that encodes Sema3A, regardless of the cell type from which it was transcribed. In particular Sema3A may be produced by a first cell type but may accumulate in a second cell type, tissue, or biological fluid. For that reason, the present invention also encompasses the mere accumulation of Sema3A, which refers to the accumulation of the protein or the mRNA.

Semaphorin 3A Activity

A "Sema3A activity" or "Sema3A biological activity" is a functional property shown by the wild-type Sema3A protein in vivo. This includes a pro-apoptotic activity, more particularly on neuronal cells, or the ability of inducing withdrawal of nerve growth cone.

As used herein, the term "neuronal cell" means neurons or any cell of the nervous system that are committed to develop into a neuron. Any type of neuronal cell may be used to assay the activity of Sema3A, such as sensory neuronal cells, sympathetic neurons or Dorsal Root Ganglion neurons (DRG). Neuronal progenitor cells may be used as well.

Sema3A activity also encompasses the binding of Sema3A to its receptor and/or activation thereof.

The Sema3A activity may be assessed by any standard method well-known by one skilled in the art, as described below:

Collapse assay. Growth cone collapse assays are described in Luo et al., Cell 1993; 75:217-227, as well as in Gagliardini et al., Molecular and Cellular Neuroscience 1999; 14:301-316, or in the International patent application WO 01/18173. In brief, neuronal cells, such as E18 mouse DRG neurons or sympathetic neurons, are allowed to extend neurites in an appropriate medium. Sema3A is then added to the cells, for about 35-45 minutes at 37° C. The cultures are fixed in 4% paraformaldehyde in PBS containing 10% sucrose. The tips of neurites without lamellipodia or filopodia are scored as being collapsed.

Neuron survival assays. The pro-apoptotic effect of a protein such as Sema3A may be assayed by treating neuronal cells with serial dilutions of the protein in the presence of trophic factors, and determining the percentage of neuronal survival before and after treatment, as described for example in Deckwerth et al., Dev. Biol. 1994; 165:63-72 or Eckenstein et al., Neuron 1990; 4:623-631. For example, cultures are incubated with additives for 24 hours before fixation, staining with a dye, and photography using an epifluorescence microscope. TUNEL staining may be performed with the ApopTag Plus kit (Talron, Israel) according to the manufacturer's protocol. Other methods, such as the fluorescent MTT assay and trypan-blue exclusion assay described in Zilkha-Falb et al., Cell. Mol. Neurobiol. 1997; 17:101-118, also may be useful. Alternatively, nuclei, especially in the form of pycnotic nuclei, may be visualized by using nuclear dye such as propidium iodide (that reveals clumped DNA). In addition, DNA laddering may be analyzed by Southern Blot techniques, or modifications in the gene expression of pro- or anti-apoptotic proteins such as Bcl, Bcx, or caspases, also may be analyzed.

Diagnostics

As used herein, the term "diagnosis" refers to the identification of the disease (i.e., AD or PD) at any stage of its development, and also includes the determination of predisposition of a subject to develop the disease. In a preferred embodiment of the invention, diagnosis of AD or PD in a subject occurs prior to the manifestation of symptoms. Subjects with a higher risk of developing the disease are of particular concern. The diagnostic method of the invention also allows confirmation of AD or PD in a subject suspected of having AD or PD.

The method of the invention comprises assessing the level of expression, accumulation or activity of Sema3A in a test subject and comparing it to the level of expression, accumulation or activity of Sema3A in a control subject (i.e., a subject not having or pre-disposed to developing the disease). An increase of expression, accumulation or activity of Sema3A in the test subject compared to the control subject is indicative of AD or PD in the test subject.

The diagnostic methods of the invention may preferably be performed in vitro, in a biological sample of a test subject, which is compared to a control sample.

A "biological sample" is any body tissue or fluid likely to contain Sema3A protein or mRNA or down-stream effectors thereof. Such samples preferably include blood or a blood component (serum, plasma), as well as cerebrospinal fluid (CSF).

The components for detecting Sema3A protein or nucleic acids can be conveniently provided in a kit form. In its simplest embodiment, such a kit provides a Sema3A detector, e.g., a detectable antibody (which may be directly labeled or which may be detected with a secondary labeled reagent), or a nucleic acid probe or a primer pair.

Nucleic Acid Based Assays

In one embodiment, the determination of the level of expression, or accumulation of Sema3A encompasses the use of nucleic acid sequences such as specific oligonucleotides to detect the presence of mRNA that encodes Sema3A nucleic acid in a biological sample.

For that purpose, one skilled in the art may use hybridization probes in solution hybridizations and in embodiments employing solid-phase procedures. In embodiments involving solid-phase procedures, the test nucleic acid is adsorbed or otherwise affixed to a selected matrix or surface. The fixed, single-stranded nucleic acid is then subjected to specific hybridization with selected probes.

In another embodiment, one skilled in the art may use oligonucleotide primers in an amplification technique, such as a reverse-PCR ("reverse polymerase chain reaction"), to specifically amplify the target mRNA potentially present in the biological sample.

As used herein, the term "oligonucleotide" refers to a nucleic acid, generally of at least 10, preferably at least 15, and more preferably at least 20 nucleotides, preferably no more than 100 nucleotides, that is hybridizable to an mRNA molecule that encodes Sema3A gene. Oligonucleotides can be labeled, e.g., with $^{32}$P-nucleotides or nucleotides to which a label, such as biotin, has been covalently conjugated. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Protein Based Assays

As an alternative to analyzing Sema3A nucleic acids, one can evaluate Sema3A on the basis of protein expression, or accumulation.

In a preferred embodiment, Sema3A is detected by immunoassay. For example, Western blotting permits detection of the presence or absence of Sema3A. Other immunoassay formats can also be used in place of Western blotting, as described below for the production of antibodies. One of these is ELISA assay.

In ELISA assays, an antibody against Sema3A or epitopic fragment thereof is immobilized onto a selected surface, for example, a surface capable of binding proteins such as the wells of a polystyrene microtiter plate. After washing to remove incompletely adsorbed polypeptides, a non-specific protein, such as bovine serum albumin (BSA), is added to block the nonspecific adsorption sites on the immobilizing surface and thus reduce the background caused by nonspecific bindings of antisera onto the surface. The immobilizing surface is then contacted with a test sample, and evaluated for immune complex (antigen/antibody) formation. This step may involve diluting the sample with diluents, such as solutions of BSA, bovine gamma globulin (BGG) and/or phosphate buffered saline (PBS)/Tween. The sample is then incubated for about 2 to 4 hours, at temperatures in the range of about 25° to 37° C. Following incubation, the sample-contacted surface is washed to remove non-bound material. The washing procedure may involve washing with a solution, such as PBS/Tween or borate buffer. Following washing, immunocomplex formation may be determined and quantitated by subjecting the immunocomplex to a second antibody specific for Sema3A, which recognizes a different epitope on the protein. To provide detecting means, the second antibody may have an associated activity such as an enzymatic activity that will generate, for example, a color development upon incubating with an appropriate chromogenic substrate. Quantitation may then be achieved by measuring the degree of color generation using, for example, a visible spectra spectrophotometer.

Typically the secondary antibody is conjugated to an enzyme such as peroxidase and the protein is detected by the addition of a soluble chromophore peroxidase substrate such as tetramethylbenzidine followed by 1 M sulfuric acid. The test protein concentration is determined by comparison with standard curves.

These protocols are detailed in Current Protocols in Molecular Biology, V. 2 Ch. 11 and Antibodies, a Laboratory Manual, Ed Harlow, David Lane, Cold Spring Harbor Laboratory 1988, pp 579-593.

Alternatively, a biochemical assay can be used to detect expression or accumulation of Sema3A, e.g., by the presence or absence of a band by polyacrylamide gel electrophoresis; by the presence or absence of a chromatographic peak using any of the various methods of high performance liquid chromatography, including reverse phase, ion exchange, and gel permeation; by the presence or absence of Sema3A in analytical capillary electrophoresis chromatography, or any other quantitative or qualitative biochemical technique known in the art.

The immunoassays discussed above involve using antibodies directed against the Sema3A protein or fragments thereof. The production of such antibodies is described below.

Anti-Semaphorin 3A Antibodies

Antibodies that specifically bind to Sema3A include but are not limited to polyclonal, monoclonal, chimeric, single chain, Fab fragments, and those within Fab expression libraries.

Various procedures known in the art may be used for the production of polyclonal antibodies to Sema3A polypeptides or derivatives or analogs thereof. For the production of antibodies, various host animals can be immunized by injection with the antigenic polypeptide, including but not limited to rabbits (described infra) mice, rats, sheep, and goats.

For preparation of monoclonal antibodies directed toward the Sema3A polypeptides, any technique that provides for the production of antibody molecules by continuous cell lines in culture may be used. These include but are not limited to the hybridoma technique originally developed by Kohler and Milstein (Nature 256:495-497, 1975), as well as the trioma technique, the human B-cell hybridoma technique (Kozbor et al., Immunology Today 1983; 4:72; Cote et al., Proc. Natl. Acad. Sci. U.S.A. 1983; 80:2026-2030), and the EBV-hybridoma technique to produce human monoclonal antibodies (Cole et al., in Monoclonal Antibodies and Cancer Therapy, Alan R. Liss, Inc. 1985, pp. 77-96). In an additional embodiment of the invention, monoclonal antibodies can be produced in germ-free animals (International Patent Publication No. WO 89/12690).

According to the invention, techniques described for the production of single chain antibodies (U.S. Pat. Nos. 5,476, 786 and 5,132,405 to Huston; U.S. Pat. No. 4,946,778) can be adapted to produce the Sema3A polypeptide-specific single chain antibodies. Indeed, these genes can be delivered for expression in vivo. An additional embodiment of the invention utilizes the techniques described for the construction of Fab expression libraries (Huse et al., Science 1989; 246: 1275-1281) to allow rapid and easy identification of monoclonal Fab fragments with the desired specificity for a Sema3A polypeptide, or its derivatives, or analogs.

Antibody fragments which contain the idiotype of the antibody molecule (anti-idiotypic antibodies) can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

Screening for the desired antibody can be accomplished by numerous techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Indirect Semaphorin 3A Activity Assays

The activity of Sema3A may be indirectly assayed by evaluating the level of expression, accumulation or activity of down-stream effectors of Sema3A such as MAP1B, CRMP-2, Rac1, or Plexins A1 and A2, and Neuropilin 1. MAP1B, CRMP-2, Rac1 are the preferred targets. Most of these effectors are reviewed in Goshima et al., Jpn. J. Pharmacol., 2000, 82:273-279, which is hereby incorporated by reference herein.

Kinases of about 40-44 kDa and 110-120 kDa detected by SDS-PAGE in association with Sema3A in AD patients, as shown in Example 1, may useful targets as well.

The nucleic acid-based assays or protein-based assays as described above may be readily adapted for indirect screening. Alternatively, the level of activity of proteins such as MAP1B, CRMP-2, or Plexin A1 may be assessed by determining the level of phosphorylation of the proteins, which is indicative of their activated state.

Phosphorylation Assays. The levels of phosphorylation of proteins can be assessed by various methods, including immunoassays or radiolabeling.

In a preferred embodiment, phosphorylation state of a protein is assessed by utilizing a binding partner, which should preferably be highly specific for the phosphoepitope on the target protein. In preferred embodiment, the binding partner is an antibody that has been generated against a unique epitope of the substrate. In an alternative embodiment, the binding partner is specific for the phosphorylated form of the target protein. The detection procedure used to assess the phosphorylation state of the protein may, for example, employ an antibody or a peptide that recognizes and binds to phosphorylated serines, threonines or tyrosines. The detection antibody is preferably a polyclonal antibody to maximize the signal, but may also be specific monoclonal antibodies which have been optimized for signal generation.

Alternatively, immunoassays may be replaced by the detection of radiolabeled phosphate according to a standard technique. This involves incubating cells with the test substances and radiolabeled phosphate, lysing the cells, separating cellular protein components of the lysate using as SDS-polyacrylamide gel (SDS-PAGE) technique, in either one or two dimensions, and detecting the presence of phosphorylated proteins by exposing X-ray film.

The phosphorylation of a protein may also be conveniently detected by migration on an electrophoresis gel followed by immunodetection, i.e., Western blotting, to determine whether a shift of the molecular weight of the protein occurs; a phosphorylated protein being heavier than the corresponding non-phosphorylated form.

In Vivo Diagnostics

The direct assays of Sema3A expression, accumulation or activity may be preferably performed in vitro, since Sema3A is a secreted protein that can be easily detected in any biological sample such as blood or CSF.

In vitro assays can be performed for down-stream effectors as well, insofar as they can be detected in such biological samples.

Alternatively, and especially when the targeted protein or mRNA cannot be easily detected by collecting a biological sample such as blood or CSF, but only possibly by a brain biopsy for instance, or when such protein or mRNA is in too small amounts for in vitro assay sensibility, in vivo diagnostic method can then be contemplated.

In vivo diagnostics especially refers to in vivo imaging methods, which permit the detection of a labeled probe or antibody that specifically hybridizes or binds Sema3A mRNA or protein, respectively, in the subject's brain. Such methods include magnetic resonance spectroscopy, positron-emission tomography (PET) and single photon emission tomography (SPECT). For purposes of in vivo imaging, the type of detection instrument available is a major factor in selecting a given label. For instance, radioactive isotopes and paramagnetic isotopes are particularly suitable for in vivo imaging. The type of instrument used will guide the selection of the radionuclide. For instance, the decay parameters of a chosen radionuclide chosen must be detectable by the selected instrument. However, any conventional method for visualizing diagnostic imaging can be utilized in accordance with this invention. In one embodiment, a radionuclide may be bound to an antibody either directly or indirectly by using an intermediary functional group. Intermediary functional groups which are often used to bind radioisotopes which exist as metallic ions to antibody include diethylenetriaminepentaacetic acid (DTPA) and ethylene diaminetetracetic acid (EDTA). Examples of metallic ions suitable as radioactive isotopes include $^{99}$mTc, $^{123}$I, $^{131}$I, $^{111}$In, $^{97}$Ru, $^{67}$Cu, $^{67}$Ga, $^{125}$I, $^{68}$Ga, $^{72}$As, $^{89}$Zr, and $^{201}$Tl. Examples of paramagnetic isotopes, particularly useful in Magnetic Resonance Imaging ("MRI"), include $^{157}$Gd, $^{55}$Mn, $^{162}$Dy, $^{52}$Cr, and $^{56}$Fe.

Screening Methods

The present invention further contemplates a screening method for identifying lead compounds that exhibit an inhibitory activity towards a Sema3A signaling complex. According to the invention, such compounds are useful in the prevention or treatment of AD or PD.

A "lead compound" is a test substance which has been shown to exhibit an inhibitory activity towards a Sema3A signaling complex.

A "test substance" or "test compound" is a chemically defined compound or mixture of substances (as in the case of a natural extract or tissue culture supernatant), whose ability to inhibit Sema3A activity may be defined by various assays Test compounds may be screened from large libraries of synthetic or natural substances. Numerous means are currently used for random and directed synthesis of saccharide, peptide, and nucleic acid based substances. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech 1996, 14:60).

Inhibitors of Sema3A activity encompass direct inhibitors of Sema3A, as well as inhibitors of down-stream effectors of Sema3A, such as MAP1B, CRMP-2, Rac1, Plexins A1 and A2, or Neuropilin 1.

The methods described below with regard to the identification of Sema3A inhibitor may be easily adapted to identify inhibitors that target Sema3A effectors.

In one embodiment, the screening method of the invention comprises (a) contacting a cell with the test substance and Sema3A under conditions wherein addition of Sema3A alone induces apoptosis of the cell; and (b) observing the effect of addition of the test substance and Sema3A to the cell, in comparison with the effect of addition of Sema3A alone to a control cell, wherein inhibition of apoptosis of the test cell compared to the control cell is indicative of a substance useful in the prevention or treatment of AD or PD. The cell may advantageously be a neuronal cell. This assay may be performed for example as described above, (see "Neuronal survival assays").

In another embodiment, the screening method of the invention comprises (a) contacting a neuronal cell with the test substance and Sema3A under conditions wherein addition of Sema3A alone induces withdrawal of the nerve growth cone; and (b) observing the effect of the addition of the test substance and Sema3A to the cell, in comparison with the effect of addition of Sema3A alone to a control cell, wherein inhibition of withdrawal of the nerve grown cone in the test cell compared to the control cell is indicative of a substance useful in the prevention or treatment of AD. Here again, this assay may be performed for example as described above ("Collapse assay").

In still another embodiment, the screening method of the invention comprises determining the effect of the test substance on the binding or activation of Sema3A receptor by Sema3A, wherein an antagonist effect of the test substance indicates that the substance is useful in the prevention or treatment of AD or PD.

This antagonist effect may be determined by an in vitro method using a recombinant Sema3A-reporter gene promoter activity system.

Reporter genes for use in the invention encode detectable proteins, include, but are by no means limited to, chloramphenicol transferase (CAT), β-galactosidase (β-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

An antagonist screen according to the invention involves detecting expression of the reporter gene by the host cell when contacted with a test substance. If there is no change in expression of the reporter gene, the test substance is not an effective antagonist. If reporter gene expression is reduced or eliminated, the test substance has inhibited Sema3A-mediated gene expression, and is thus a candidate for development of an AD or PD therapeutic.

The reporter gene assay system described here may be used in a high-throughput primary screen for antagonists, or it may be used as a secondary functional screen for candidate compounds identified by a different primary screen, e.g., a binding assay screen that identifies substances that modulate Sema3A transcription activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred. Alternatively, simple reporter-gene based cell assays such as the one described here are also highly desirable.

Intact cells or whole animals expressing a gene encoding Sema3A can be used in screening methods to identify candidate drugs or lead compounds.

In one series of embodiments, a permanent cell line is established. Alternatively, cells are transiently programmed to express a Sema3A gene by introduction of appropriate DNA or mRNA.

Identification of candidate compounds can be achieved using any suitable assay, including without limitation (i)

assays that measure selective binding of test substances to Sema3A (ii) assays that measure the ability of a test substance to modify (i.e., inhibit) a measurable activity or function of Sema3A and (iii) assays that measure the ability of a substance to modify (i.e., inhibit) the transcriptional activity of sequences derived from the promoter (i.e., regulatory) regions of the Sema3A gene.

Useful substances are typically those that bind to Sema3A or disrupt the association of Sema3A with its receptor (e.g., Neuropilin 1/Plexins complexes, see WO 99/04263 or WO 01/18173).

Alternatively useful substances may be screened for their ability to block processing or secretion of Sema3A, especially by interfering with Sema3A cleavage site.

In Vivo Models

In a specific embodiment of the screening method of the invention, the inhibitory effect of the substance is determined in vivo, by administering the substance to an animal that shows a level of Sema3A protein greater than that of a control animal. Although rats and mice, as well as rabbits, are most frequently employed, particularly for laboratory studies, any animal can be employed in the practice of the invention.

This animal may be a transgenic animal that overexpresses Sema3A. This transgenic animal may be considered as a model animal for AD or PD. The production of such transgenic animal is described in further detail below.

Transgenic Animals. The term "transgenic" usually refers to animal whose germ line and somatic cells contain the transgene of interest, i.e., Sema3A gene. However, transient transgenic animals can be created by the ex vivo or in vivo introduction of an expression vector that encodes Sema3A. Preferred expression vectors are viral vectors, such as lentiviruses, retroviruses, herpes viruses, adenoviruses, adeno-associated viruses, vaccinia virus, baculovirus, alphavirus, influenza virus, and other recombinant viruses with desirable cellular tropism. Thus, a gene encoding Sema3A can be introduced in vivo using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication WO 95/28494.

Both types of "transgenic" animals are contemplated for use in the present invention, e.g., to evaluate the effect of a test substance on Sema3A expression, accumulation or activity.

Animals overexpressing Sema3A may be produced by introducing a Sema3A gene in an endogenous locus. This can be achieved by homologous recombination, transposition (Westphal and Leder, Curr Biol 1997; 7:530), using mutant recombination sites (Araki et al., Nucleic Acids Res 1997; 25:868) or PCR (Zhang and Henderson, Biotechniques 1988; 25:784). See also, Coffman, Semin. Nephrol. 1997; 17:404; Esther et al., Lab. Invest. 1996; 74:953; Murakami et al., Blood Press. 1996; Suppl. 2:36.

Generally, for homologous recombination, the DNA is at least about 1 kilobase (kb) in length and preferably 3-4 kb in length, thereby providing sufficient complementary sequence for recombination when the construct is introduced. Transgenic constructs can be introduced into the genomic DNA of the ES cells, into the male pronucleus of a fertilized oocyte by microinjection, or by any methods known in the art, e.g., as described in U.S. Pat. Nos. 4,736,866 and 4,870,009, and by Hogan et al., *Transgenic Animals: A Laboratory Manual*, 1986, Cold Spring Harbor. A transgenic founder animal can be used to breed other transgenic animals; alternatively, a transgenic founder may be cloned to produce other transgenic animals.

Wild-Type Animals. In another embodiment, the animal that shows a level of Sema3A protein superior to a control animal is merely an animal to which Sema3A protein has been administered. Micro-injections of the protein into certain areas of the brain of the animal are more particularly contemplated within the present invention and described herein.

The animals (regardless they are transgenic or not) are administered with the substance to be tested by any convenient route, for example by systemic injection, pumps for long-term exposure, or direct intracerebral injection. These animals may be included in a behavior study, so as to determine the effect of the substance on the cognitive behavior of the animals for instance. A biopsy or anatomical evaluation of animal brain tissue may also be performed, or a sample of blood or CSF may be collected, to perform in vitro assays as described above.

Therapeutics

Inhibition of Semaphorin 3A

The present invention further provides a method for the prevention or treatment of AD, which method comprises inhibiting Sema3A expression, accumulation or activity in a subject or patient.

The method for the prevention or treatment of AD or PD comprises administering to a patient in need of such treatment an effective amount or a substance that inhibits Sema3A expression, accumulation or activity, which a pharmaceutically acceptable carrier.

A "subject" or "patient" is a human or an animal likely to develop AD or PD, more particularly a mammal, preferably a human, rodent or primate, as described above in connection with diagnostic applications.

The term "prevention" refers to the prevention of the onset of AD or PD, which means to prophylactically interfere with a pathological mechanism that results in the disease. In the context of the present invention, such a pathological mechanism can be an increase of Sema3A expression, or accumulation. The patient may be a subject that has an increased risk of developing the disease. For example, for AD, such subject may have a genetic predisposition to developing an amyloidosis, such as a person from a family that has members with familial AD (FAD). Alternatively, someone in his or her seventh or eighth decade is at greater risk for age-related AD.

The term "treatment" means to therapeutically intervene in the development or pathology of a disease in a subject showing a symptom of this disease. In the context of the present invention, these symptoms can include development of dementia, memory defects, and the like in the fifth and sixth decade.

Both prevention and treatment of AD or PD are facilitated by the neuroprotective property of the substances that inhibit Sema3A expression, accumulation or activity, especially on vulnerable neurons.

The term "therapeutically effective amount" is used herein to mean an amount or dose sufficient to decrease the level of Sema3A activity e.g., by about 10%, preferably by about 50%, and more preferably by about 90% percent. Preferably, a therapeutically effective amount can ameliorate or present a clinically significant deficit in the activity, function and effects of Sema3A. Alternatively, a therapeutically effective amount is sufficient to cause an improvement in a clinically significant condition in the subject to which it is administered.

The inhibition of Sema3A expression, accumulation or activity may be achieved by various methods, as described hereafter.

In one embodiment, the inhibition may be directed against Sema3A protein or against any of its down-stream effectors, such as MAP1B, CRMP-2, Rac1, Plexins A1 and A2 or Neuropilin-1. The methods discussed below may be easily adapted to perform the latter embodiment.

In another embodiment, the inhibitory substance may be a substance that is known or has been identified to compete with Sema3A for binding to its receptor. Vascular Endothelial Growth Factor-165 (VEGF-165), shown to compete with Sema3A for binding to Neuropilin-1 (NRP-1), is more particularly encompassed (Soker et al., Cell 1998; 92:735-745; Bagnard et al., The Journal of Neuroscience 2000; 10: 332-3341).

Alternatively, this inhibitory substance may be a candidate drug as identified by the screening methods discussed above.

Selected inhibitory agents may be modified to enhance efficacy, stability, pharmaceutical compatibility, and the like. For example, where peptide antagonists are identified, they may be modified in a variety of ways, e.g. to enhance their proteolytic stability. Structural identification of an agent also may be used to identify, generate, or screen additional agents.

The inhibitory substance may be an antibody that is directed against Sema3A. Antibodies that block the activity of Sema3A may be produced and selected according to any standard method well-known by one skilled in the art, such as those described above in the context of diagnostic applications.

In another embodiment, the substance that inhibits the Sema3A protein is an antisense nucleic acid specific for Sema3A mRNA. An "antisense nucleic acid" is a single stranded nucleic acid molecule which, on hybridizing under cytoplasmic conditions with complementary bases in an RNA or DNA molecule, inhibits translation or transcription. If the RNA is a messenger RNA transcript, the antisense nucleic acid is a countertranscript or mRNA-interfering complementary nucleic acid. "Antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607). The substance that inhibits Sema3A may also be an antisense nucleic acid specific for a downstream effector in the Sema3A signaling pathway. Antisense therapy is discussed in more detail below.

Formulations and Administration

The substance that inhibits Sema3A activity is advantageously formulated in a pharmaceutical composition, with a pharmaceutically acceptable carrier. This substance may be then called active ingredient, or therapeutic agent, against AD or PD.

The concentration or amount of the active ingredient depends on the desired dosage and administration regimen, as discussed below. Suitable dose ranges may include from about 1 mg/kg to about 100 mg/kg of body weight per day.

The pharmaceutical compositions may also include other biologically active substances in combination with the Sema3A inhibitory agents. Such substances include but are not limited to donepezil hydrochloride (Aricept®), rivastigmine tartrate (Exelon®), galantamine (Reminyl®), tacrine (Cognex®), and non-steroidal anti-inflammatory drugs (NSAIDs).

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the substance is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

According to the invention, the pharmaceutical composition of the invention can be introduced parenterally, transmucosally, e.g., orally (per os), nasally, rectally, or transdermally. Parental routes include intravenous, intra-arteriole, intramuscular, intradermal, subcutaneous, intraperitoneal, intraventricular, and intracranial administration.

The pharmaceutical compositions may be added to a retained physiological fluid such as blood or synovial fluid. For CNS (Central Nervous System) administration, a variety of techniques are available for promoting transfer of the therapeutic across the blood brain barrier including disruption by surgery or injection, co-administration of drugs which transiently open adhesion contact between CNS vasculature endothelial cells, and co-administration of substances which facilitate translocation through such cells.

In another embodiment, the active ingredient can be delivered in a vesicle, in particular a liposome (see Langer, Science 1990; 249:1527-1533; Treat et al., in Liposomes in the Therapy of Infectious Disease and Cancer, Lopez-Berestein and Fidler (eds.), Liss: New York 1989 pp. 353-365; Lopez-Berestein, ibid., pp. 317-327; see generally ibid.).

In yet another embodiment, the therapeutic substance can be delivered in a controlled release formulation. For example, a polypeptide may be administered using intravenous infusion with a continuous pump, in a polymer matrix such as poly-lactic/glutamic acid (PLGA), a pellet containing a mixture of cholesterol and the active ingredient (SilasticR™; Dow Corning, Midland, Mich.; see U.S. Pat. No. 5,554,601) implanted subcutaneously, an implantable osmotic pump, a transdermal patch, liposomes, or other modes of administration.

Antisense Therapy. In another embodiment, vectors comprising a sequence encoding an antisense nucleic acid according to the invention may be administered by any known methods, including methods used for gene therapy that are available in the art. Exemplary methods are described below. For general reviews of the methods of gene therapy, see, Goldspiel et al., Clinical Pharmacy 1993, 12:488-505; Wu and Wu, Biotherapy 1991, 3:87-95; Tolstoshev, Ann. Rev. Pharmacol. Toxicol. 1993, 32:573-596; Mulligan, Science 1993, 260:926-932; and Morgan and Anderson, Ann. Rev. Biochem. 1993, 62:191-217; May, TIBTECH 1993, 11:155-215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley & Sons, NY.

In one embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, Proc. Natl. Acad. Sci. USA 1989, 86:8932-8935; Zijlstra et al., Nature 1989, 342:435-438).

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

In a specific embodiment, the vector is directly administered in vivo, where it enters the cells of the organism and mediates expression of the construct. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-1-4-N-acetylglucosamine polysaccharide; see, U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, J. Biol. Chem. 1987, 62:4429-4432), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., Mol. Therapy 2000, 2:339-47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188).

EXAMPLES

The present invention is also described by means of particular examples. However, the use of such examples anywhere in the specification is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims, along with the full scope of equivalents to which the claims are entitled.

Example 1

Isolation of a Sema3A Signaling Complex in Hippocampal Neurons During Alzheimer's Disease Methods Immunoaffinity purification of a multiprotein complex. Hippocampal fields were isolated from brain of patients with overt AD (CDR3-5) at autopsy, and frozen. Samples from 6 cases were pulverized in liquid nitrogen and dissolved in buffer A (50 mM HEPES [pH 7.4]; 50 mM NaCl; 10 mM EDTA; 0.5% Triton X-100) supplemented with 100 µg/ml leupeptin, 10 µg/ml bacitracin, 100 µg/ml aprotinin, 100 µg/ml bis-benzamide, 1 mM $Na_3VO_4$, and 10 mM—glycerophosphate. Dissolved tissue was extracted by gentle shaking for 1 hour at 4° C., then clarified by centrifugation (30,000× g). Centrifuge step was repeated and the supernatant was recovered.

A rabbit polyclonal antibody was generated against the phosphorylated peptide PP172 (IYSYQWMALT*PVVKC-SEQ ID NO: 1; asterisk indicates phosphorylated residue) according to methods well known in the art. Non-phospho-specific antibodies were depleted by column chromatography using same peptide lacking phosphate (P172). Specific antibodies then were affinity purified by column chromatography using the phosphorylated peptide. The antibodies were bound to protein A-agarose, washed, then coupled covalently to the column with dimethyl pimelimidate. The column washed with several volumes of buffer A prior to use.

The lysate was pre-incubated with protein A-agarose bead (lacking antibody) to absorb non-specific binding proteins. Following removal of these beads, the lysate was incubated overnight with protein A-agarose beads coupled to PP172 antibody at 4° C. while gently mixing). The next day the beads were collected by centrifugation, then transferred to a column and washed with several volumes of buffer A. Proteins were eluted from the beads with 1 mg/ml PP172 peptide.

Eluted proteins were resolved by SDS-PAGE, and either stained with Coomassie blue or processed for Western blot with PP172 antibody using standard methods. Proteins stained by Coomassie blue were excised from the gels and washed with 50% acetonitrile. Nine independent gel regions were excised and sequence analysis was performed at the Harvard Microchemistry Facility, by microcapillary reverse-phase HPLC nano-electrospray tandem mass spectrometry (mLC/MS/MS) on a Finnigan LCQ quadrupole ion trap mass spectrometer. The method provides high sensitivity (<10 femtomole) but does not allow an estimation of the relative abundance of the peptides. The MS/MS spectra (fragmentation spectra) were correlated with known sequences using an algorithm (Sequest; Eng, et al., Am. Soc. Mass Spectrom 1994, 5:976-989) and programs developed in the Harvard Microchemistry Facility (Chittum, et al., Biochemistry 1998, 37:10866-70).

Kinase activity assay and immunoaffinity purification. The multiprotein complexes isolated above were incubated with 10 µCi $\gamma^{32}$P-ATP in Buffer A supplemented with 25 mM $MgCl_2$ (final concentration of ATP, 50 µM). Reactions were stopped after 30 minutes (37° C.) by the addition of EDTA to 50 mM. Samples were resolved by SDS-PAGE and visualized by autoradiography (exposure times of 12 and 48 hours are shown). Bands migrating at 190, 125, and 65 kDa that are phosphorylated were observed. The apparent masses of these bands correspond to those previously observed to be phosphorylated in vitro in samples immunoaffinity purified from neurons using a CRMP-2 antibody (Kamata, et al., Molecular Brain Research 1998, 54:219-36).

A polyacrylamide gel was co-polymerized with histone H1, and PP172 antibody affinity-purified protein complexes were resolved and renatured by SDS-PAGE through this gel. Next, an in situ assay for histone H1 kinase activity was performed as described (Carter, in *Current Protocols in Molecular Biology*, F. M. Ausubel, et al., Eds., John Wiley and sons, New York, 1998, pp. 18.7.1-18.7.22). The gel was then dried and phosphorylated histone H1 was detected by autoradiography.

Western blot analysis of PP172 antibody immunoaffinity-purified protein complexes was performed. The multiprotein complex immunoaffinity-purified by PP172 antibody was resolved by SDS-PAGE, transferred to a nitrocellulose membrane, and analyzed by Western blot with antibodies against Plexin A1 (A1) and Plexin A2 (A2), purchased from Santa Cruz Biotechnology.

Detection of CRMP-2 and Sema3A. Protein complexes were immunoaffinity purified with PP172 antibody as described above from hippocampal samples derived from patients with no evidence of disease or from patients with overt AD. Complexes were resolved by SDS-PAGE and silver stained. Bands visualized in Coomassie blue stained gels were identified by mass spectroscopy as CRMP-2.

The samples described above also were analyzed by Western blot with an antibody to Sema3A (Santa Cruz; antibody H300). In addition, total homogenates of normal aged human hippocampus and thalamus were evaluated for the presence of Sema3A using the H300 antibody.

Results

A rabbit polyclonal antibody was generated against a synthetic phosphorylated peptide containing the sequence surrounding a proline directed kinase site on cyclin-dependent kinase 4 (peptide 172 [P172]; phosphorylated peptide 172 [PP172]; Matsuoka, et al., Molecular and Cellular Biology 1994, 14:7265-75). The antibody was affinity-purified and depleted so that it bound exclusively the phosphorylated form of the peptide. To determine the identity of the neuronal antigen recognized by PP172 antibody, hippocampal samples from patients with advanced AD were obtained at autopsy, homogenized, and immunoaffinity purified. Bound antigens were eluted from the columns using the phosphopeptide antigen (PP172).

A multi-protein complex was eluted from the immunoaffinity columns by competition with PP172 peptide, was resolved by SDS-PAGE, and stained with Coomassie Blue. Several of the protein components of this complex that were detected by Coomassie Blue stain were extracted from the gels and identified by peptide digestion and nuclear magnetic resonance (NMR) analysis (Table 1).

TABLE 1

Mass Spectroscopic Identification of Components in a Multiprotein Complex Immunoaffinity Purified from Hippocampus of Patients with AD

| Migration Rate (kDa): | Peptides: |
|---|---|
| 125 | MAP1B (p.f.) |
| 62 | MAP1B (p.f.) |
| 60 | CRMP-2 |
| 59 | CRMP-2 |
| 56 | CRMP-2(p.f.) |
| 54 | CRMP-2 (p.f.) |
| 50 | CRMP-2 (p.f.) |

TABLE 1-continued

Mass Spectroscopic Identification of Components in a Multiprotein Complex Immunoaffinity Purified from Hippocampus of Patients with AD

| Migration Rate (kDa): | Peptides: |
|---|---|
| 49 | CRMP-2 (p.f.); α-tubulin; β-tubulin; Vacuolar H+-ATPase |
| 42 | Actin; α-centractin; GFAP; Tau protein; Synapsin IIa; Synapsin IIb; CRMP-2 (p.f.) |

Abbreviations:
MAP1B, microtubule-associated protein 1B;
CRMP-2, collapsin response mediator protein-2;
GFAP, glial fibrillary acidic protein; and
p.f., proteolytic fragment (smaller than full length protein).

As shown in Table 1, in addition to an abundance of CRMP-2, several other polypeptides were detected in the complex. To determine which component(s) were bound by PP172 antibody, Western blot analysis was performed on the eluted complex. The antibody bound several bands, two of which were identified by mass spectroscopy. The larger of these bands migrates at approximately 120 kDa, and was identified as a proteolytic fragment of MAP1B. In addition, another band that bound PP172 antibody and migrated slightly slower than the major CRMP-2 band (approximately 60 kDa) was also identified as a proteolytic fragment of MAP1B. Careful alignment of the PP172 antibody Western blot with a Coomassie stained gel ran in parallel revealed that the antibody bound the slower migrating MAP1B fragment but did not bind the major CRMP-2 band. Together, these data indicate that PP172 binds the MAP1B component of the complex. Incubation of antibody with phosphopeptide or digestion of the proteins on the nitrocellulose membrane with bacterial alkaline phosphatase prior to Western blot analysis virtually eliminated antibody binding, suggesting that the MAP1B epitope(s) bound by PP172 antibody are phosphorylated.

The other immunoaffinity purified proteins detected by Coomassie stain did not bind PP172 antibody in Western blot analysis, and therefore must be directly or indirectly associated with MAP1B through a multiprotein complex. CRMP-2 is abundant in this complex, although whether it is bound to phosphorylated MAP1B or another protein component is not clear from these studies. Members of the CRMP family have been shown to form homotypic and heterotypic tetramers (Wang, et al., J. Neurosci. 1996, 16:6197-207); hence, the abundance of CRMP-2 in the immunoaffinity purified protein complex may be disproportionate to its binding partner(s). In addition, evidence has been reported that CRMP-2 may interaction with tubulin and/or microtubules (Gu and Ihara, J. Biol. Chem. 2000, 275:17917-20). Immunoaffinity purified CRMP-2 from PC12 cells has been shown to be associated with a kinase activity that phosphorylates coprecipitating 190 kDa, 125 kDa (a proteolytic fragment of the 190 kDa protein), 65 kDa (phosphorylated CRMP-2), and 35 kDa proteins (Kamata et al., Molecular Brain Research 1998, 54:219-36). Similarly, incubation of the PP172 antibody immunoaffinity purified complex with $\gamma^{32}$P-ATP and $MgCl_2$ resulted in phosphorylation of 190 kDa, 125 kDa, and 65 kDa bands. In PC12 cells, phosphorylation of these proteins is enhanced two to three-fold by treatment of the cells with nerve growth factor (NGF; Kamata, et al., Molecular Brain Research 1998, 54:219-36), suggesting a role in signal transduction. In order to determine the positions of associated kinases, PP172 antibody immunoaffinity complexes were resolved by SDS-PAGE and analyzed in situ for kinase activity using histone H1 as a substrate. The migration positions of two potential kinase activities were identified at 40-44 kDa and 110-120 kDa.

Members of the CRMP family, such as CRMP-2, have been shown to be involved in transduction of signals from Sema3A (Goshima, et al., Nature 1995, 376:509-14; Nakamura, et al., Neuron 1998, 21:1093-100). Since this protein is a major component of the PP172 antibody affinity purified protein complex, Western blot analyses were performed to determine whether the transmembrane Sema3A receptor components also present. The receptor for Sema3A consists of at least two associated transmembrane proteins: Neuropilin-1 and Plexin A1/A2 (Takahashi et al., Cell 1999, 99:59-69; Yu and Kolodkin, Neuron 1979, 22:11-4; Rohm, et al., Mechanisms of Development 2000, 93:95-104). Since the transmembrane domain of Neuropilin-1 is not required for association with Plexin A1/A2 and the generation of an active complex, signal transduction from the complex is thought to be mediated by the Plexin(s), which have a tyrosine kinase activity associated with their cytoplasmic domain (Tamagnone and Comoglio, Trends Cell. Biol. 2000, 10:377-83). Although other semaphorins can use plexins alone as their receptors, Sema3A requires Plexin A1/A2 and Neuropilin-1 to signal growth cone collapse (Takahashi et al., Cell 1999, 99:59-69; Yu and Kolodkin, Neuron 1999, 22:11-4; Rohm, et al., Mechanisms of Development 2000, 93:95-104). Western blot analysis detected both Plexin A1 and A2 in the PP172 antibody immunoaffinity purified transduction complex from patients with advanced AD.

Surprisingly, intact Neuropilin-1 was not detected in the PP172 immunoprecipitated complexes by Western blot using two commercially available antibodies (Santa Cruz Biotechnology) and a polyclonal anti-serum. There are several possible explanations for this: 1) The antibodies are not high affinity or do not have high specificity for Neuropilin-1; 2) Neuropilin-1 is part of the receptor complex on the cell surface, but after internalization is cycled out of the complex independently of the Plexins; 3) An unidentified functional homolog of Neuropilin-1 is expressed in the brains of AD patients; or 4) During affinity purification of the complex, the epitope(s) are removed from Neuropilin-1 by proteolysis. In support of the latter possibility, experiments from other laboratories have shown that the activity of the Neuropilin-1/Plexin A1 receptor complex is maintained using a deletion mutant lacking the Neuropilin-1 transmembrane domain (Nakamura, et al., Neuron 1998, 21:1093-100). In addition, the inventors have detected in some Western blots a 55 kDa band that binds Neuropilin-1 antibody, and it is possible that this represents a proteolytic fragment that is functionally sufficient to mediate Sema3A binding in the PP172 antibody immunoaffinity purified complexes. Consistent with this interpretation, preliminary immunohistochemical studies have detected Neuropilin-1 staining in the hippocampus of disease-free and AD patients.

Further experiments were performed to compare the protein components of immunoaffinity purified complexes from AD brains with those purified from age-matched brains without disease. Hippocampal samples collected at autopsy were homogenized, and immunoaffinity purified with PP172 antibody. Equivalent quantities of total immunoprecipitated protein from AD brains and brains without disease were analyzed by SDS-PAGE and silver stain. The most prominent difference between the silver stain profiles was in the intensity of the bands identified by mass spectrometry as CRMP-2 and proteolytic fragments of CRMP-2.

Western blot analysis of the antibody P172 immunoaffinity purified complexes revealed a strong signal for Sema3A in the samples isolated from AD patients. The protein recognized by the Santa Cruz H300 antibody was identified as human Sema3A. Western blots of total homogenates of normal aged human hippocampus and thalamus reveal bands consistent with that reported in the literature (data not shown). The band at 90 kDa in hippocampus (H) represents the active, secreted form of the human Sema3a protein as reported in the literature. The bands at 120 kDa in both hippocampus and thalamus represent the uncleaved, inactive, membrane associated protein and the higher molecular weight proteins at 160 kDa represent posttranslational processing forms of the protein. In addition, the H300 antibody also recognizes purified, recombinantly expressed Sema3A (data not shown). The antibody detected Sema3A migrating at approximately 90 kDa, the molecular mass of the active form of the secreted protein (Adams, et al., EMBO J. 1997, 16:6077-86). Together, these data indicate that the complexes from AD patients contain the active form of the Sema3A ligand and have recruited CRMP-2, features of a functional signaling complex.

Example 2

Detection of Sema 3A by Immunocytochemistry on AD Brain Sections

Methods

Isolation and preparation of samples. AD and age matched control cases were derived from the Mount Sinai Alzheimer's Disease Research Center (ADRC) Brain Bank. All cases have been characterized for cognitive status by a clinical dementia rating (CDR) at a maximum time interval of one year prior to death. The clinical testing results in a clinical dementia rating score for each individual. This score ranges from CDR0: cognitively normal; CDR0.5 questionable; CDR1, mild; CDR2, moderate; CDR3, severe; CDR4, profound; CDR5, terminal. Ten CDR0 cases: mean age at death 77.9±10.7 yr (s.d.), post mortem interval (pmi): 289.4±103.4 min; 5 CDR0.5 cases, mean age 80.6±10.1 yr, pmi 869.4±1310 min (1 case pmi 3485 min); 19 CDR 1-3 cases, mean age 87.9±8.84 yr, pmi 421.8±406.2 min; 15 CDR 5 cases, mean age 83±11.8 yr, pmi 336.9±178.7 min.

The brains of individuals participating in the ADRC are removed at minimal post-mortem intervals and hemisected in the mid-sagittal plane, one half is fixed in 4% paraformaldehyde and on half is sub-dissected into brain regions, snap frozen and stored at −70° C. Post mortem intervals range from a minimum of 180 minutes to 24 hours. Cases are received in the Mount Sinai Neuropathology Research Laboratory after a whole-brain fixation interval of two to three weeks. Hippocampal blocks are dissected from the temporal lobe, washed, equilibrated in 30% sucrose and sectioned at 50 µM.

Immunocytochemistry. Immunocytochemistry is performed on floating sections using an antibody that recognizes a phosphorylated form of microtubule associated protein, PP172 at 1:40,000 dilution prepared under contract by New England Biolabs, an antibody raised against a peptide specific to human Sema3A (epitope corresponding to amino acids 103-402 mapping to the conserved extracellular semaphorin domain of SEMA 3A of human origin) commercially available from Santa Cruz Biotechnology at 1:500, and an antibody that recognizes abnormally phosphorylated MAP tau that occurs in AD at 1:5,000. Between the primary labels, excess biotin was blocked with Vector Avidin-Biotin blocking kit (Vector, Burlingame Calif.) and unreacted peroxidase was removed by treatment with 1% hydrogen peroxide. Biotinylated secondary antibodies (Vector) of the appropriate species were followed by Vector elite avidin biotin peroxidase. Peroxidase substrate chromophores used were diaminobenzidine (DAB) and Vector SG.

Frozen tissues are transported on dry ice and stored at −70° C. until processed. From the frozen hippocampal block the hippocampal formation consisting of dentate gyrus, hippocampus proper and subiculum are dissected while remaining frozen and processed for biochemical studies.

Results

In cognitively normal individuals, PP172 immunolabeling of a phosphorylated MAP1B epitope was seen rarely, as described above. Where immunolabeling was evident, it occurred within neurons at the CA3/CA1 border, as single or multiple discrete perikaryal puncta, as well as appearing in isolated neurons in CA1 and subiculum. In these cases immunolabeling was never seen in the dentate gyrus (DG) or CA3.

With increasing severity of clinical dementia rating (CDR) score the numbers of neurons demonstrating immunoreactivity increased dramatically. In addition the numbers and size of granules increased and the granules took on a vesicular morphology rather than that of discrete puncta. In the most severely affected cases, in addition to the large vesicular structures, immunoreactivity was found spread across the neuropil of the pyramidal neuron layer of CA1, no longer confined only to identifiable neuronal profiles. In these severe of AD cases, PP172 labeling of CA3 and DG was seen in just a small number of neurons.

To determine if the presence of the PP172 immunoreactivity was a generalized phenomenon or was confined to the hippocampal formation, sections of parahippocampal gyrus, superior temporal gyrus and primary visual cortex of CDR5 cases were immunolabeled with the PP172 antibody. In each of these three areas, labeling similar to that seen in CA1 and subiculum was seen. In STG such labeling could be seen in both deep and superficial layers while in V1 the labeling was primarily confined to infragranular layers.

To examine the relationship between the upregulation of PP172 and neurofibrillary tangles, sections were double labeled with PP172 and AD2 (Buee-Scherrer, et al., Brain Res. Mol. Brain Res. 1996, 39(1-2):79-88) an antibody that recognizes abnormally phosphorylated, paired helical filament associated tau (PHF-tau). In a large number of neuronal profiles colocalization of PP172 with AD2 was seen. In some neurons the direct apposition of PP172 and AD2 immunoreactivity was seen.

The demonstration of an association between PP172 and CRMP-2 discussed in Example 1 implied that human Sema 3A (hSema 3A) could be associated with the immunoprecipitated complex as well. Immunolabeling of AD cases and age matched cognitively normal cases with an antibody generated against a peptide fragment specific to hSEMA 3A (Santa Cruz Biotechnology) demonstrated the presence in CDR0 cases of hSEMA 3A in CA3 at the CA3/CA1 border, confined to a relatively small population of pyramidal neurons, and displaying a faint to moderate density of immunoreactivity (FIGS. 1A to 1C). Some CDR0 cases demonstrated a more intense immunolabeling of the CA3 neurons but such labeling was confined to CA3 and ended abruptly at the CA1 border.

With progression of disease the immunolabeling became more intense, the numbers of labeled neurons increased and were found throughout CA1 and subiculum (FIGS. 1D to 1F). In the most advanced cases of AD (FIGS. 1G to 1I) the hSEMA 3A immunolabeling took on a vesicular appearance both within CA1 neurons as well as in the neuropil surrounding the remaining CA1 neurons.

To establish the relationship between the presence of semaphorin immunoreactivity and neurofibrillary degeneration, double labeling studies combining anti-hSEMA 3A and AD2 immunolabeling were performed. Many neurons within CA1 and subiculum were double labeled with others showing immunoreactivity for only one or the other of the markers.

To determine the relationship between the presence of semaphorin immunoreactivity and that of PP172, double labeling studies combining the anti-hSEMA 3A antibody and PP172 were performed. In these cases both markers were present in many neurons. In 5 μM paraffin sections the hSEMA 3A immunoreactivity was present filling a portion of the perinuclear soma while granules of PP172 immunoreactivity were present within the pool of hSEMA 3 immunoreactivity.

Figure 2:
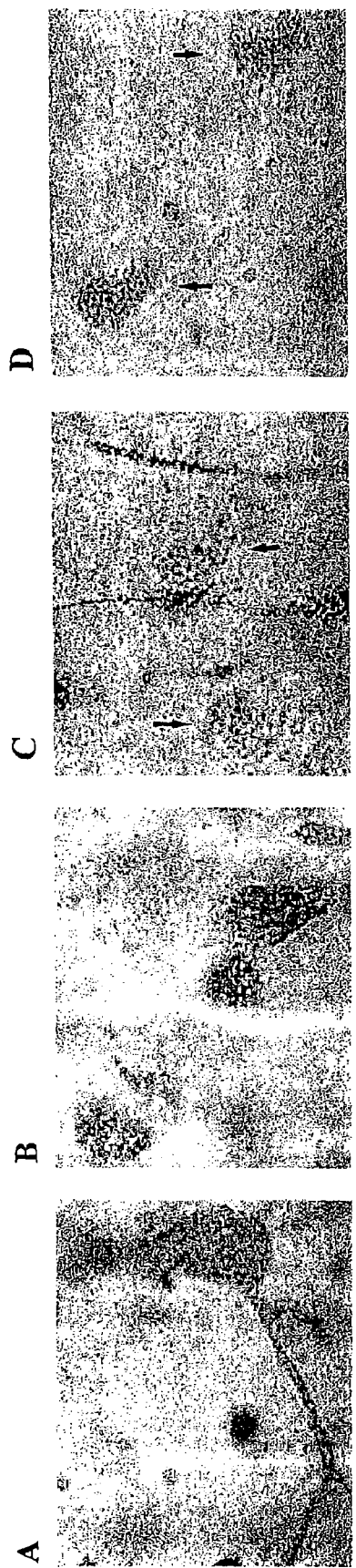
FIGS. 2A-D show Sema 3A immunolabeling of hippocampus and thalamus tissue derived from cognitively normal, age matched cases acquired from the Mount Sinai AD research center, isolated from a patient with PD.

It was also demonstrated that the hSema3A protein can assume two distinct morphological distributions associated with the neuronal populations of either the hippocampus or thalamus: a "dendritic" form (FIG. 2A) in which the Sema3A immunoreactivity coats the surfaces of the dendrites of the hippocampus and is not seen in a perikaryal distribution, and an internalized form (FIG. 2B) in which there is dense granular perinuclear immunoreactivity in the absence of dendritic labeling. Since the dendritic labeling is identified in the thalamus in a dendritic distribution in the lateral dorsal nucleus (FIG. 2C), but not in a perikaryal distribution in either this small thalamic nucleus or in the ventral nuclear group (FIG. 2E), and the molecular weight seen in the thalamus is exclusively the size known to be the unprocessed pro-protein (120 kDa), it appears that the active, 95 kDa form is that which is seen internalized in the hippocampus and the 120 kDa pro-protein form is the dendritic form, the only form identified in the thalamus.

Discussion

The data presented here provide powerful evidence that the accumulation of hSEMA 3A, CRMP-2 and phospho-MAP1B in an activated signal transduction complex is a central event leading to neurodegeneration in AD.

In AD, phospho-MAP1B and hSEMA 3A appear as colocalized markers in an intimate intraneuronal relationship in CA1 and subiculum; the two hippocampal fields most highly vulnerable to AD related neurodegeneration. Phospho-MAP1B and hSEMA 3A appear together at the earliest stages of AD in CA1 at the CA3 border, and progress to a presence within large numbers of neurons throughout CA1 and subiculum. In addition to these two components, CRMP-2 and an unknown kinase activity capable of phosphorylating histone H1 are also present, forming an activated signal transduction complex.

The appearance of hSEMA 3A and phospho-MAP1B in neurons both without and with neurofibrillary tangles implies that the formation of the signal transduction complex is a primary and transient phenomenon. Abnormally phosphorylated tau, a major component of NFTs is present within neurons at early stages of the neurodegenerative process (Buee-Scherrer, et al., Brain Res. Mol. Brain Res. 1991, 39(1-2):79-88) and persists well past the demise of the neuron, forming extracellular or ghost tangles. The presence of phospho-MAP1B and hSEMA 3A in neurons without NFTs implies that the complex forms before the appearance of NFTs. The colocalization of elements of the complex in direct apposition to PHF-tau provides evidence that the kinase component of the complex phosphorylates tau, generating PHF-tau that persists past the loss of morphological evidence of PP172 and hSEMA 3A.

The appearance of both phospho-MAP1B and hSEMA 3A as immunoreactivity spread across the pyramidal cell layer of CA1 and not specifically localized to neuronal profiles implies that the complex may be released from neurons, possibly to be taken up by neighboring neuronal processes whereupon they may be capable of initiating the neurodegenerative process in a second order of neurons. Such a scheme makes it possible to explain the well-described spread of neurodegeneration among the association cortices with direct connectivity to the hippocampal formation (Braak, et al., Eur. Neurol. 1993, 33(6):403-8).

In addition, identified herein is a second morphological distribution of Sema3A, associated with the cell membranes of the dendritic arbor of neurons in the human hippocampus. This distribution is termed the "dendritic" form as contrasted with the "somatic" or perikaryal distribution initially identified. The dendritic distribution has also been identified in the human thalamus, in the absence of the intense perikaryal somatic accumulation seen in the AD hippocampus. The dendritic distribution identified in the thalamus is associated only with the 125 kDa immunoreactive Sema3A bands on Western blot of thalamus, where the active, 95 kDa form is absent, leading to the conclusion that the dendritic form is the 125 kDa membrane associated pro-protein form of Sema3A identified by Adams et al., EMBO J 1997 16(20): 6077-86. In the hippocampus, both the 95 and 125 kDa forms are present, implying that the somatic form is the 95 kDa active form used by investigators described above to induce apoptosis in neuronal culture.

Example 3

Detection of Sema3A by Immunocytochemistry on PD Brain Sections and Evaluation of Intracellular Effectors of Sema3A Signaling in PD Analytical approach. Melanized neurons and single and double-labeled neurons are counted and expressed as total numbers, and percentages of melanized neurons for each case. tissue sections for Sema3A and Map1B, Sema3A and p38, and Sema3A and -synuclein will be double-labeled. The hypothesis is that Sema3A signaling is the event that initiates the neurodegenerative cascade, therefore, the most informative procedure is to co-localize Sema3A with the putative downstream effectors to determine the relative expression of phospho-MAP1B, phospho-p38 and α-synuclein in association with Sema3A. Although the proposed sample size is relatively small it is anticipated that as disease progresses, as quantified by increasing neuronal loss, there will be a greater recruitment of the downstream markers, phospho-MAP1B and phospho-p38 and α-synuclein positive inclusions. Linear regressions correlating melanized neuron number and expression of pathological markers will be calculated.

Methods

Isolation and preparation of samples. Tissues were derived from patients at the Mt. Sinai Alzheimer's Disease Research Center and Jewish Home Project, who have been extensively characterized both clinically and pathologically. Although this facility is dedicated to the investigation of AD, specimens of cortex, substantia nigra and other subcortical regions of PD, Incidental Lewy Body Disease and PD/AD disease overlap cases are available. All donated specimens in this repository are brain-banked; one hemisphere is dissected and frozen and one is fixed in paraformaldehyde. The midbrain and hippocampus were routinely processed from all cases received in the laboratory for stereological analysis. The midbrain and hippocampus were carefully dissected from the fixed hemisphere as separate blocks encompassing the entire structures. The midbrain was dissected with a transverse cut, rostrally at the level of the mammilary bodies and caudally at the upper pons ensuring the entire structure is available for study. Brainstems were further blocked into 3.2 mm slabs and alternate slabs were cryoprotected and serial sectioned at 100 μM. The resulting 32 sections were stored in storage solution (a mixture of glycerol and ethylene glycol in phosphate buffered saline) and held at −20° C.

For immunoprecipitation, midbrain substantia nigra specimens are obtained from brains of patients with pathological diagnosis of PD, including Lewy body formation and incontinent melanin, and from age matched control cases, and transported frozen to the laboratory.

Immunocytochemistry. The following antibodies are used: Sema3A, Neuropilin-1, Plexin A1 and A2 (Santa Cruz Biotechnology, Santa Cruz, Calif.), phospho-p38 (Cell Signaling Technology, Beverly, Mass.), MAP1B (antibody MPM2, Upstate Biotechnology, Lake Placid, N.Y.) (in addition to PP172) and α-synuclein (Chemicon, Temecula, Calif.). CRMP-2 antibodies are not commercially available and immunoassays for CRMP-2 levels will require generation of antibodies detecting CRMP-2. A hemagglutinin-tagged fusion protein has been generated from a CRMP-2 clone (Wang et al., J Neurosci 1996; 16(19): 6197-207). This protein will be used for production of rabbit polyclonal antibodies.

Sections of substantia nigra were incubated overnight with primary anti-Sema 3A antibody H300 (Santa Cruz) at a 1:500 dilution or with primary antibody PP172 at a 1:40,000 dilution as described above, followed by incubation with a biotinylated secondary antibody raised against the immunoglobulins of the species in which the primary antibody was raised, e.g., anti-Sema H300 was raised in rabbit, the secondary antibody is a biotinylated anti-rabbit IgG raised in goat. Visualization occurred by blue-gray SG chromophore, no counterstain.

For staining for Neuorpilin-1, Plexin A1 and A2, MAP1B, CCR2, phospho-p38 and -synuclein, floating sections were incubated in the primary antibody overnight at room temperature, followed by incubation with a biotinylated secondary antibody of the appropriate species, followed by treatment with substrates avidin-biotin peroxidase and chromophore. A number of chromophores easily distinguishable from neuromelanin are available such as Vector SG (blue-gray shown herein), VIP (purple), etc. Double labeling of tissues for Sema 3A and Map1B, Sema 3A and -synuclein, and Sema 3A and p38, will be performed sequentially with the first primary incubated overnight and developed through chromophore treatment the following day. After development, unreacted peroxidase is exhausted by 3% peroxide in methanol and unbound biotin is blocked with Vector avidin-biotin blocking kit. The second antibody will then be processed in the same manner. If two primary antibodies raised in the same species are used, an additional blocking step with normal serum, binding any remaining antibody will be used. To ensure specificity, controls reversing the order of the primaries and omitting the second primary with an alternative secondary antibody/alkaline phosphatase/substrate system will be used. This control should be negative for immunolabeling.

Stereology. Stereology is performed using an Olympus Bx61 microscope equipped with MicroBrightField Stereo Investigator. Specifically, the fractionator and optical dissector techniques integral to this software will be applied. Objects of interest in each disector are counted according to the criteria of inclusion or exclusion of the dissector. From the consideration of the fraction of the total volume of the substantia nigra sampled the total number of neurons positive for a marker or combination of markers is calculated (West et al., Anat Record 1991; 231:482-497).

Immunoprecipitation and Western blotting. Midbrain substantia nigra specimen samples are pulverized over liquid nitrogen and dissolved in buffer A (50 mM HEPES, pH 7.4, 50 mM NaCl; 10 mM EDTA; 0.5% Triton X-100) supplemented with 100 μg/ml leupeptin, 10 μg/ml bacitracin, 100 μg/ml aprotinin, 100 μg/ml bis-benzamide, 1 mM Na3VO$_4$, and 10 mM a-glycerophosphate. Dissolved tissue is extracted by gentle shaking for 1 hour (4° C.), and then clarified by centrifugation (30,000×g). Centrifuge step is repeated and the supernatant is recovered.

The midbrain lysate is pre-incubated with protein A agarose beads (lacking anti-body) to pre-absorb non-specific binding proteins. After removal of the beads, the lysate is incubated overnight with protein A-agarose beads coupled to PP172 antibody at 4° C. with gentle mixing. The next day, the beads are collected and washed with several volumes of buffer A. Proteins are eluted from the beads with 1 mg/ml PP172 peptide. Eluted proteins are resolved by SDS-PAGE, and either stained with Coomassie blue or process for Western blotting using antibodies specific for Semaphorin, CRMP-2, Neuropilin-1, PlexinA1 and A2, and p38. Midbrain homogenates that are not pre-immunoprecipitated with the PP172 antibody will also be analyzed by Western blotting for the above-mentioned proteins. If necessary, protein microsequence analysis will be performed by the Harvard Microchemistry Facility.

Rat Brain Injections. Animals are briefly restrained for anesthesia, and anesthesia is induced by i.p. injection of chloral hydrate (400 mg/kg). Animals are placed in a Kopf stereotaxic surgery apparatus. A 1-2 mm craniotomy is made with a surgical burr at a point above the left substantia nigra (+2.9 mm A-P, +2.1 mm L from intra-aural 0, −7.5 mm from dura). A 26G Hamilton syringe needle is then introduced into the left substantia nigra and 50 or 500 ng in 500 mL of selected protein(s) is introduced into the substantia nigra. The needle will remain in place for five minutes to allow the pressure to equilibrate. The needle is then withdrawn, the craniotomy closed with bone wax and the skin sutured with nylon. Topical analgesic is administered and the animals allowed to recover. Animals will survive for one week and are sacrificed by overdose of carbon dioxide and decapitated. The brain is rapidly removed and fixed in 4% paraformaldehyde for further analysis. Three different agents, will be evaluated, semaphorin alone, semaphorin combined with CRMP-2 at a 1:1 weight ratio and CRMP-2 alone with endpoints of one week. Midbrain sections will be immunolabeled for tyrosine hydroxylase for dopaminergic neurons and studied by stereological assay of numbers of surviving neurons.

Results

Figure 3:
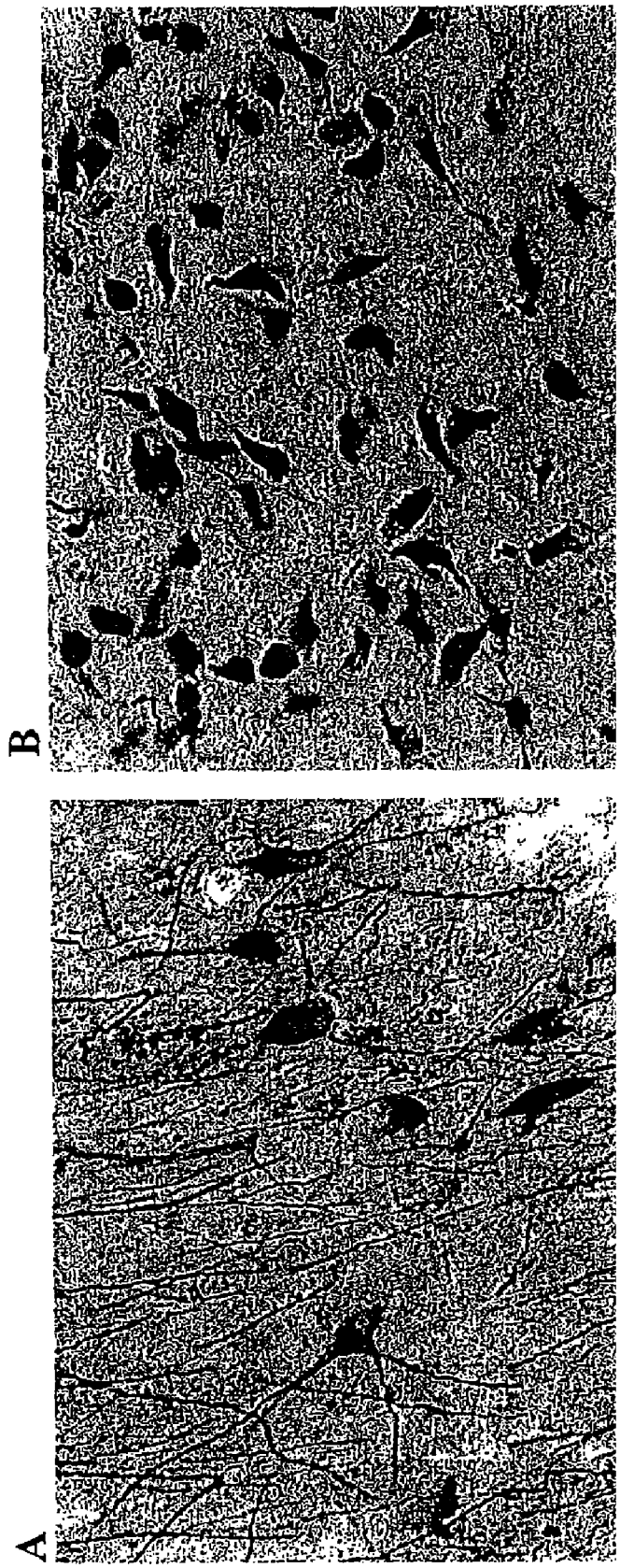
FIGS. 3A-B show Sema 3A immunolabeling of PD (FIG. 3A) and control (FIG. 3B) substantia nigra as detected by the PP172 MAP1B-specific antibody. Both the somatic (arrows) and dendritic (arrowheads) immunolabeling of melanized neurons are shown. Antigen is visualized by blue-gray SG chromophore (20× magnification); the dark area represents neuromelanin. Somatic immunolabeling indicates a dense granular region of immunoreactivity confined to the region immediately adjacent to the nucleus (perikaryal labeling), without any labeling of the dendritic arbor. In comparison, the dendritic pattern of labeling is distributed along the surfaces of the dendritic arbor with a less intense, frequently faint labeling on the membrane surrounding the cell body.

Initially supporting the hypothesis that upregulation of Semaphorin and CRMP-2 are coincident with the induction of apoptosis of neurons, these results demonstrate a striking accumulation of Sema3A in substantia nigra pars compacta (SNc) melanized neurons, compared with an absence of Sema3A in age-matched controls (FIG. 3). FIG. 3A demonstrates immunolabeling of a PD case in which both the soma and dendrites of melanized neurons are immunolabeled (i.e., somatic and dendritic staining). FIG. 3B shows the absence of labeling in the control sample.

Figure 4:
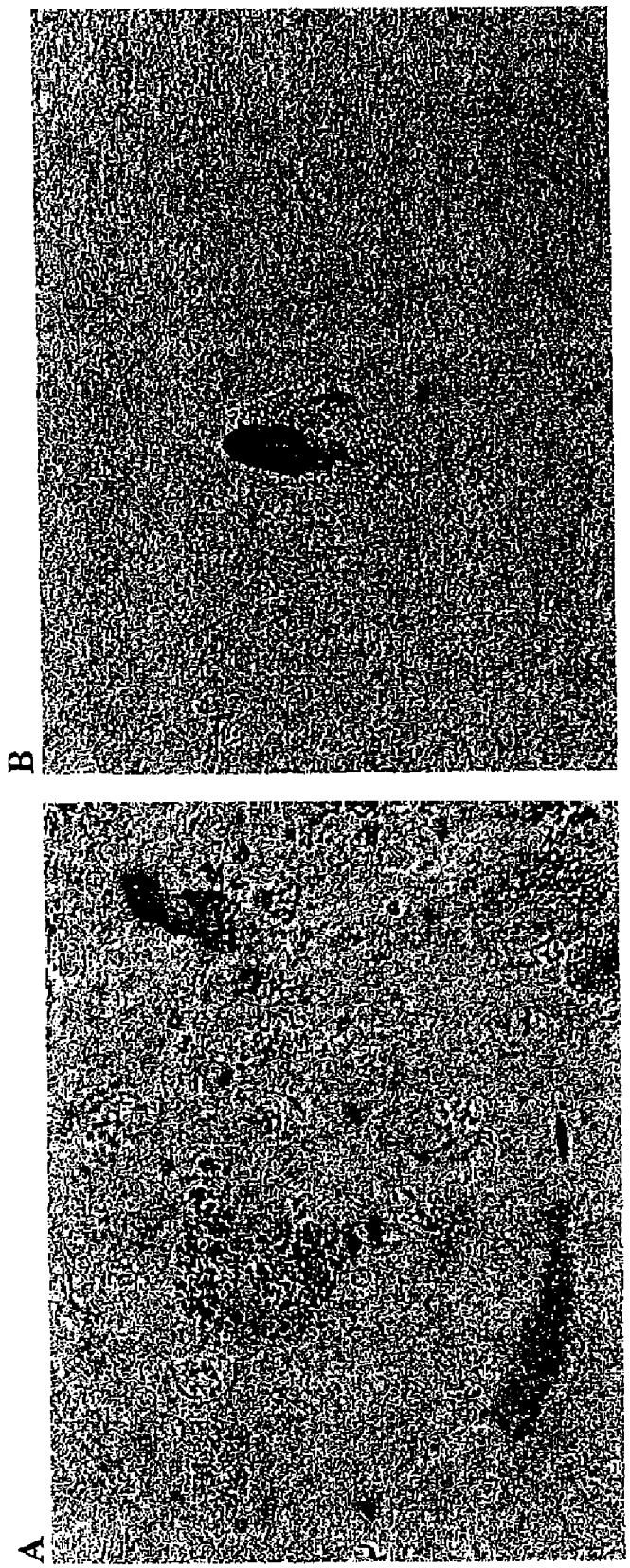
FIGS. 4A-B show Sema 3A immunolabeling of PD and substantia nigra with the PP172 antibody (40× magnification).

In addition, punctate inclusions immunolabeled by PP172 were identified in the degenerating SNc of PD, similar to results observed in AD (FIG. 4) PP172 also recognized ovoid structures with the unambiguous morphology of Lewy bodies (FIG. 4B). Such inclusions are not seen in age-matched controls (FIG. 4A).

Figure 5:
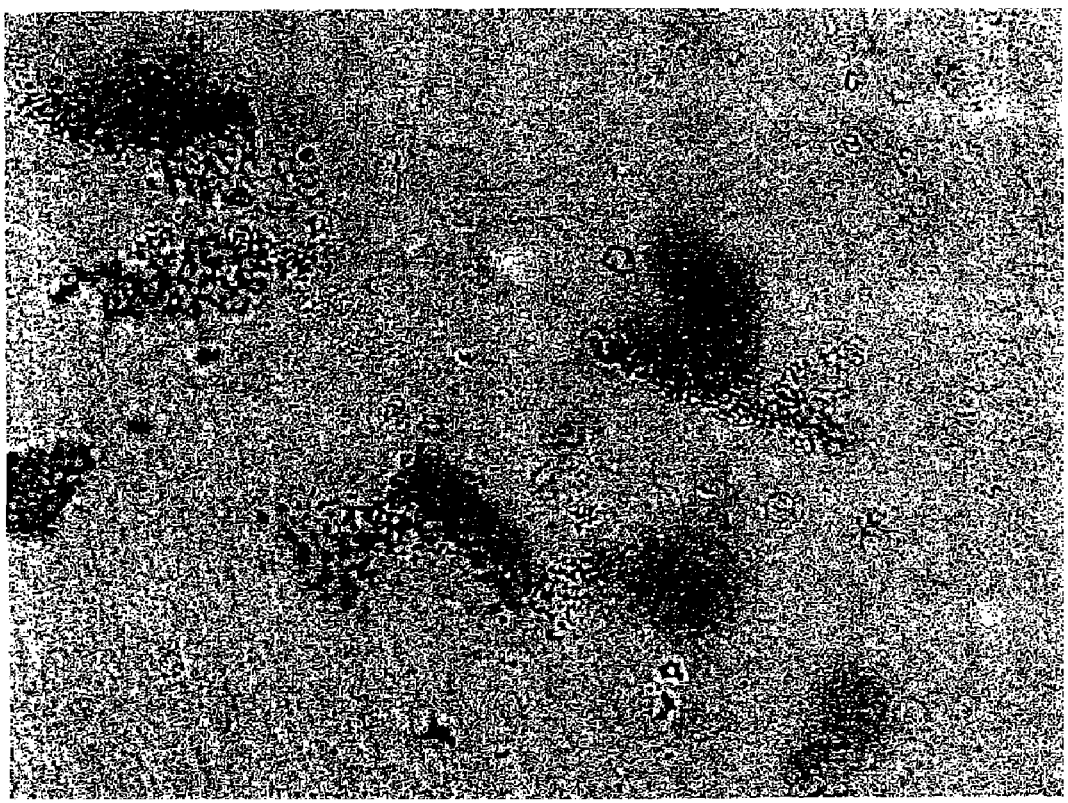
FIG. 5 shows immunolabeling of PD specimens with an antibody that recognizes activated p38. Antigen is visualized by blue-gray SG chromophore—the dark area represents neuromelanin (60× magnification).

Further, the activated p38 kinase was seen as punctate inclusions within SNc neurons while absent from age-matched controls (FIG. 5), confirming the observations of Ferrer et al. (Ferrer et al., J Neural Transm 2001; 108:1383-96). These data corroborate the demonstration of a link among dopamine induced oxidative stress, Sema3A and CRMP-2 upregulation, and p38 and caspase activation shown by Junn and Mouradian, who showed the activation of p38 and apoptotic signaling following a dopamine challenge of SH-SY5Y neuroblastoma cells (Junn and Mouradian, J Neurochem 2001; 78:374-83).

For further investigation, the intracellular effectors of the semaphorin pathway will be examined for complex assembly with Sema3A and upregulation, similar to that demonstrated above for AD. Currently archived for examination are samples from six cases with pathological diagnosis of PD, two cases of PD/diffuse Lewy body disease, and two AD/PD overlap cases. Frozen substantia nigra from the midbrain of five PD cases and five controls will be separately assayed by Western blot and pooled for immunoprecipitation and further analysis.

Although the sample size is small, it is anticipated that as the disease progresses, correlating with increased neuronal loss, there will be a greater recruitment of the downstream markers phospho-MAP1B and phospho-p38 and α-synuclein positive inclusions. It is also anticipated that an increase in the colocalization of Sema3A with downstream effectors will correlate with the progression of the disease. Control cases may give indications of these parameters in the earliest stages of PD as well. These studies will test the hypothesis that the upregulation of Sema3A precedes the expression of MAP1B, p38 and -synuclein positive inclusions and neuronal loss.

To test the hypothesis that Sema 3A can directly cause substantia nigra neurodegeneration, Sema 3A, Sema 3A in combination with CRMP-2 at a 1:1 weight ratio, or CRMP-2 alone will be injected into the brains of anesthetized rats. After one week, the rats will be sacrificed and their brains examined for neurodegeneration.

Discussion

The accumulation of Sema3A, phosphorylated MAP1B, and p38 inclusions specific to neurons in patients with PD, will strongly suggest that a common intracellular apoptotic pathway is activated in response to a common insult in PD and AD. It is hypothesized that the insult that initiates this cascade is the conversion of the pro-protein 125 kDa form of Sema3A to the active form, its retrograde transport to the cell body and its activation of a signal transduction pathway comprising, at a minimum, Plexins, CRMP-2 and MAP1B. In the hippocampus, the neurons expressing the greatest level of the dendritic form of Sema3A were those located in the subiculum. This area in known to be the major target of hippocampal subfield CA1, and therefore an area from which retrograde transport of Sema3A would readily take place. In PD the relationship of target neurons to those pathologically affected is less clear. It is hypothesized that either the striatum, the preferential target of the substantia nigra compacta neurons, or the substantia nigra reticulata, an adjacent region with extensive interconnections, is the region expressing the pro-protein 125 kDa form of Sema3A. Events upstream of the activation of the Sema3A pathway are less certain. Since Sema is an axon guidance molecule, it is likely that the initiation of this pathway involves synaptic disruption with the ensuing necessity of axons to reestablish synaptic contact to function normally. Such synaptic disruption is known to be one of the earliest changes seen in AD.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method for identifying a test substance useful in the treatment of Alzheimer's disease, which method comprises the following steps:
   (a) contacting a test neuronal cell with the test substance and Semaphorin 3A protein under conditions wherein the addition of the Semaphorin 3A protein alone induces withdrawal, retraction or collapse of the nerve growth cone;
   (b) contacting a control neuronal cell with the Semaphorin 3A protein alone under the same conditions;
   (c) comparing withdrawal, retraction or collapse of the nerve growth cone in the test neuronal cell of step (a) and the control neuronal cell of step (b);
   (d) identifying as a substance useful for the treatment of Alzheimer's disease the test substance which inhibits withdrawal, retraction or collapse of the nerve growth cone in the test neuronal cell of step (a) as compared to the control neuronal cell of step (b); and
   (e) administering the test compound identified as useful for the treatment of Alzheimer's disease in step (d) to an animal model of Alzheimer's disease.

2. The method according to claim 1, wherein the Semaphorin 3A is human Semaphorin 3A.

* * * * *